(12) United States Patent
Kashiwagi et al.

(10) Patent No.: US 7,438,413 B2
(45) Date of Patent: Oct. 21, 2008

(54) OPHTHALMIC IMAGE SENSING APPARATUS

(75) Inventors: Kenichi Kashiwagi, Kawasaki (JP); Kyoji Sekiguchi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 220 days.

(21) Appl. No.: 11/238,414

(22) Filed: Sep. 28, 2005

(65) Prior Publication Data
US 2006/0077344 A1   Apr. 13, 2006

(30) Foreign Application Priority Data
Sep. 29, 2004  (JP)  ............................. 2004-283468
Jun. 20, 2005  (JP)  ............................. 2005-179160

(51) Int. Cl.
*A61B 3/14* (2006.01)
(52) U.S. Cl. ..................................... 351/206; 351/205
(58) Field of Classification Search ................ 351/206, 351/205
See application file for complete search history.

(56) References Cited

U.S. PATENT DOCUMENTS

| | | | |
|---|---|---|---|
| 4,773,749 A | * | 9/1988 | Ohtomo et al. ............. 351/206 |
| 5,422,690 A | * | 6/1995 | Rothberg et al. ............ 351/209 |
| 5,909,269 A | * | 6/1999 | Isogai et al. ................ 351/208 |
| 2002/0176050 A1 | * | 11/2002 | Shibata ....................... 351/206 |
| 2003/0076477 A1 | * | 4/2003 | Matsumoto ................. 351/206 |

FOREIGN PATENT DOCUMENTS

| | | |
|---|---|---|
| JP | 10-75932 | 3/1998 |
| JP | 10-113336 | 5/1998 |

* cited by examiner

*Primary Examiner*—Ricky Mack
*Assistant Examiner*—James R Greece
(74) *Attorney, Agent, or Firm*—Morgan & Finnegan, LLP

(57) ABSTRACT

In a case of right and left eye fundus image sensing in a mass health examination, the alignment of an anterior segment of an eye to be examined is performed first (S101). When the alignment of the anterior segment of eye is completed, image sensing light intensity is set (S102). The alignment of a fundus segment of the eye to be examined is performed (S103). Furthermore, an image of the fundus of the eye to be examined is sensed by a sensing switch being pushed after the completion of focus adjustment (S104). Next, an optical base unit is moved so that the image sensing of another eye can be performed (S105). A left or right eye detection unit detects that an eye for image sensing is changed with the move of the optical base unit. When the eye for image sensing is changed, an image sensing light intensity setting unit sets image sensing light intensity by adding a predetermined amount, or changing the sets image sensing light intensity according to a diameter of a pupil (S106). Then, alignment and the like are performed similarly to S101 and S103 (S107, S108), and an image of another eye is sensed.

8 Claims, 18 Drawing Sheets

OPHTHALMIC IMAGE SENSING APPARATUS

BACKGROUND OF THE INVENTION

1. Field of the Invention

The present invention relates to an ophthalmic image sensing apparatus such as a fundus camera used in fundus examinations such as a mass health examination.

2. Related Background Art

As disclosed in Japanese Patent Application Laid-Open No. H10-75932 official gazette and Japanese Patent Application Laid-Open No. H10-113336, in mass health examinations such as a resident medical examination and a company medical examination, fundus examinations are implemented respectively. Although fundus image sensing of only one eye was performed before, since a finding may have appeared in the other eye which has not been examined, right and left eye image sensing has implemented in recent years.

In fundus image sensing in a mass health examination, non-mydriasis image sensing which does not need a mydriatic is performed usually. The non-mydriasis image sensing is performed after urging the natural mydriasis of an eye to be examined, by making the inside of an inspecting room dark, or covering a head including an eye to be examined from indoor light by a simple darkroom or the like.

In addition, although a roll of 35 mm film, a Polaroid film or the like has been used for the recording of a sensed image up to now, a method of recording as a digital image using a sensor, such as a CCD, has gone mainstream in recent years. Generally, in this digital image recording, there is an advantage that there may be low image sensing light intensity from the difference of sensitivity of image sensing apparatuses in comparison with silver halide film recording.

Hence, since there is little effect of miosis after image sensing when a digital image recording system is used, it becomes possible to sense images of right and left eyes in a shorter time in comparison with a silver halide film recording system.

However, since being non-mydriasis image sensing cannot disregard the effect of the miosis after image sensing, when right and left eye image sensing is performed continuously, there is a problem that an image of an eye to be examined which is image sensed later becomes dark. For this reason, when an image of the other eye is sensed after the completion of a first image sensing, image sensing light intensity is adjusted so that the image of the other eye may be kept from becoming dark in the former.

Thereby, there has arisen a trouble that it has been forgotten to return the adjusted light intensity in the case that another person to be examined has taken the place, or the like. In addition, also as to the adjustment intensity of image sensing light intensity, since a camera person sets it by experience, difference appears in the quality of a sensed image by the presence of experience, or even if he/she is an experienced person, it is said that it is difficult to set proper image sensing light intensity from a state of a pupil which changes with time.

As stated also in advance, usually, non-mydriasis image sensing for which the fundus image sensing mentioned above does not need a mydriatic is performed. In the non-mydriasis image sensing, a darkroom, a simple darkroom which covers only a head, including an eye to be examined, from indoor light, or the like are used, and fundus image sensing is performed with making the eye to be examined natural mydriasis. Although a roll of 35 mm film, an instant film or the like has been used for the recording of a sensed image up to now, a method of recording as a digital image using a sensor, such as a CCD, has gone mainstream in recent years. Generally, in digital image recording, there is an advantage that low image sensing light intensity is required from the difference of sensitivity of image sensing apparatuses in comparison with silver halide film recording. Hence, since there is little effect of miosis after image sensing when a digital image recording system is used, it becomes possible to sense images of right and left eyes in a shorter time in comparison with a silver halide film recording system.

In addition, in order to observe a papilla region three-dimensionally (stereoscopically) for glaucomatous diagnosis, temporal stereography of sensing two images with shifting the two images by certain baseline length within a pupil is also performed. Furthermore, in order to be able to observe a fundus image at once to a peripheral part of a fundus of an eye, it is performed to create one panorama fundus image by sensing 3 to 8 images with changing a fixation position by shifting a position of a fixation lamp of a fundus camera, and pasting the images together.

However, even if image sensing is performed in low image sensing light intensity so as to sense images in a state of non-mydriasis, it is not possible to disregard the effect of miosis after image sensing. Hence, when the image sensing of the same eye to be examined is performed continuously, the fundus images may become darker as the times increase. For this reason, it may be necessary to adjust the image sensing light intensity before next image sensing is performed after the end of a first image sensing.

In addition, also when performing solid image sensing and image sensing for panorama creation in the state of non-mydriasis, an experience may be needed for the adjustment of the image sensing light intensity due to miosis in the second image sensing rather than the first image sensing.

SUMMARY OF THE INVENTION

The present invention aims to provide a fundus image sensing apparatus which reduces an adjustment burden of image sensing light intensity.

An ophthalmic image sensing apparatus according to one aspect of the present invention for attaining the above-mentioned object has the following structure.

The ophthalmic image sensing apparatus has:

image sensing means for sensing a fundus image of an eye to be examined;

left or right eye detection means of detecting whether an eye being examined is right or left eye;

first image sensing light intensity setting means of setting light intensity at the time of image sensing by the above-mentioned image sensing means; and second image sensing light intensity setting means of setting light intensity at the time of the next image sensing by the above-mentioned image sensing means on the basis of the detection result of the above-mentioned left or right eye detection means after executing image sensing by the above-mentioned image sensing means in the light intensity set by the first image sensing light intensity setting means.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with.

DETAILED DESCRIPTION OF THE PREFERRED EMBODIMENTS

Preferred embodiments of the present invention will now be described in detail in accordance with the accompanying drawings.

The present invention will be described in detail on the basis of embodiments shown.

Embodiment 1

Figure 1:
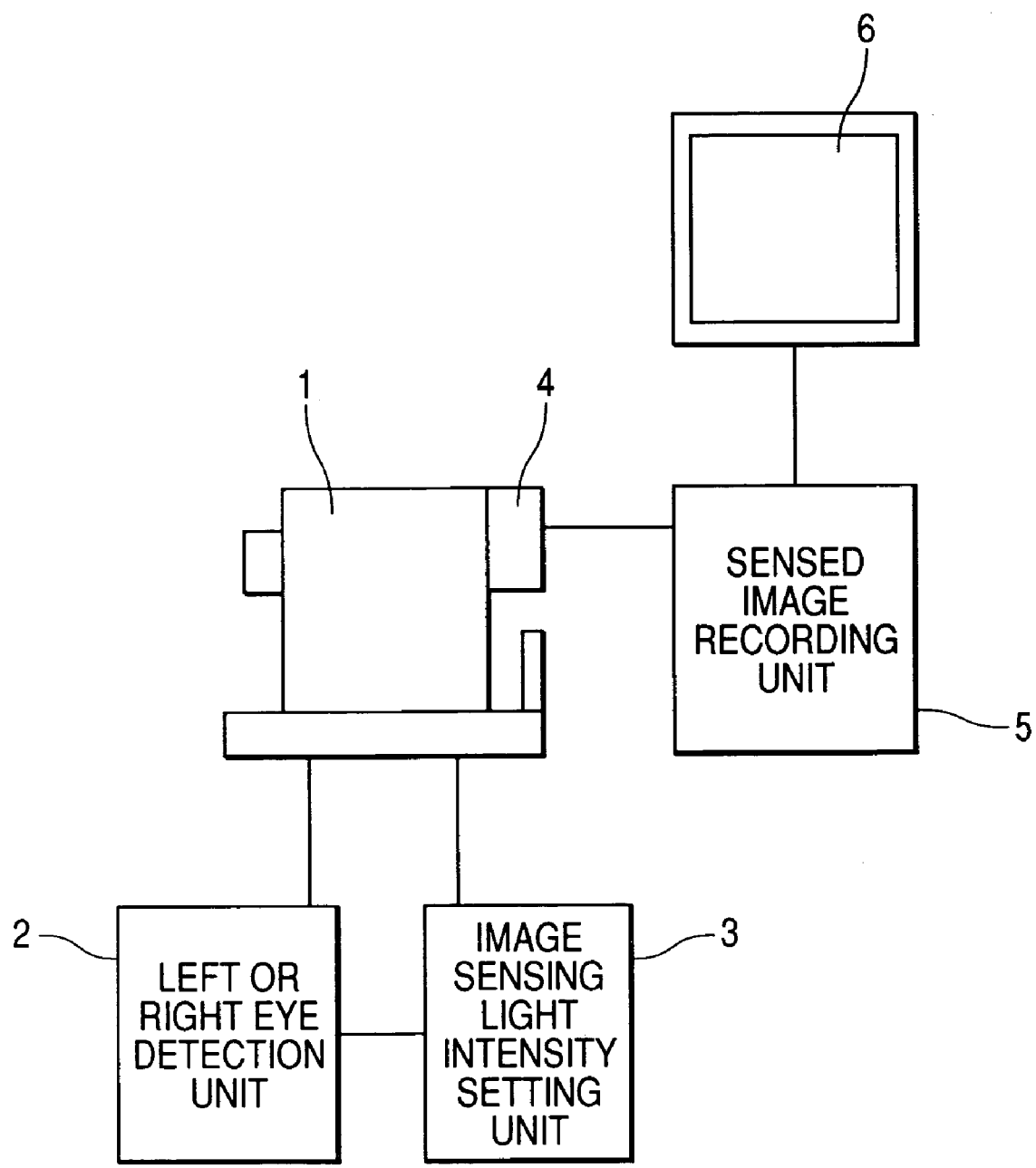
FIG. 1 being a structural diagram of an apparatus of a first embodiment.

FIG. 1 shows a structural diagram of an apparatus of a first embodiment. A left or right eye detection unit 2, an image sensing light intensity setting unit 3, and a CCD camera 4 sensing an image of a fundus of eye to be examined are added to a fundus camera 1. An output of the CCD camera 4 is connected to a sensed image recording unit 5, which records a sensed fundus image, and a monitor 6 which displays a sensed image.

Figure 2:
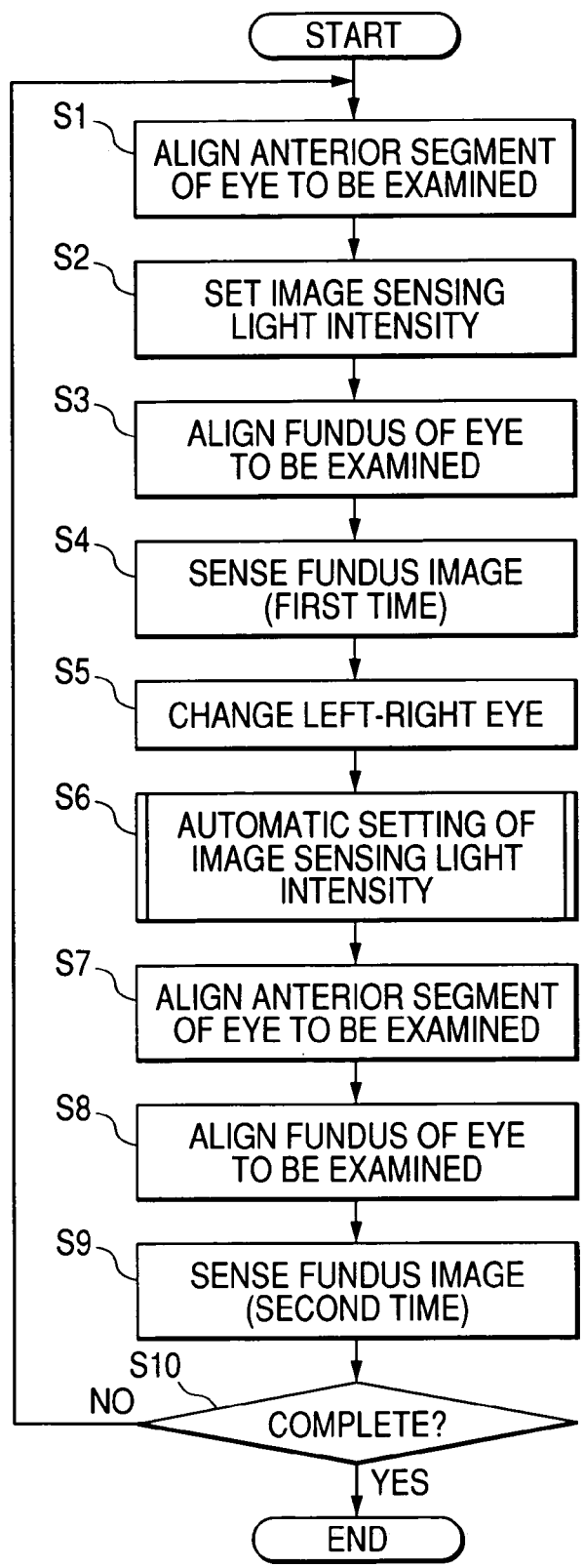
FIG. 2 being an operation flowchart of the first embodiment.

FIG. 2 is a flowchart of an execution procedure of the first embodiment. In a case of right and left eye fundus image sensing in a mass health examination, the alignment of an anterior segment of eye to be examined is performed first (step S1). This alignment of an eye to be examined is performed by illuminating an anterior segment of eye to be examined by an observing light source for an anterior segment of eye at a near-infrared wavelength in the fundus camera 1, and moving an optical base unit in the fundus camera 1 with observing an image of the anterior segment of eye which is sensed by an observation CCD camera not shown, by an observing monitor.

When the alignment of the anterior segment of eye is completed, image sensing light intensity is set (step S2). Generally, in a mass health examination, since natural mydriasis is enough performed under a darkroom environment before the first image sensing is performed, a fine adjustment of image sensing light intensity every person to be examined is unnecessary. But, when a mydriasis state is inadequate especially, image sensing light intensity is set arbitrarily.

Next, the alignment of a fundus of eye to be examined is performed (step S3). An anterior/fundus changing switch in the fundus camera 1 performs a change to a fundus observing state from an anterior observing state. When the anterior/fundus changing switch is operated, a lens in the fundus camera 1 is changed and an image sensed in an observation CCD camera is changed from an anterior segment image to a fundus image. In addition, simultaneously, an observing light source for an anterior segment of eye is turned out, and an observing light source for a fundus of eye is turned on. In addition, it is also good to constitute the transition to a fundus observing state from an anterior observing state with interlocking with the move of the optical base unit not only by the operation of the anterior/fundus changing switch.

The alignment of the fundus of eye and the distance adjustment between the fundus camera 1 and the eye to be examined are performed by illuminating the fundus of eye to be examined by an observing light source for a fundus of eye at a near-infrared wavelength in the fundus camera 1, and moving the optical base unit in the fundus camera 1 with observing an image of the fundus of eye which is sensed by an observation CCD camera, by an observing monitor.

In addition, at this time, the focus adjustment of the fundus of eye to be examined is also performed with a focus adjustment member in the fundus camera 1. An image of the fundus of eye to be examined is sensed by a sensing switch being pushed after a completion of the adjustment (step S4). When the sensing switch is pushed, a light source for image sensing, such as a xenon tube, emits light, and an image of a fundus of eye is sensed by the CCD camera 4. The sensed image data of the fundus of eye is recorded after the A/D conversion within a sensed image recording unit 5, and is simultaneously displayed also on the monitor 6 for the image sensing of any one of the right and left eyes to be completed.

Next, the optical base unit is moved so that the image sensing of another eye can be performed (step S5). The left or right eye detection unit 2 detects that an eye for image sensing changes with the move of the optical base unit. Specifically, a detection switch in the left or right eye detection unit 2 is changed by the move of the optical base unit, and it is judged on the basis of positional information of the detection switch.

In addition, it is mentioned as an example to perform left or right eye detection by the change of the detection switch caused by the move of the optical base unit as the operation of the left or right eye detection unit 2. However, it is also good to be so constituted as to perform left or right eye detection from fundus image information, such as a position of an optic disk which is obtained by the observation CCD camera, or left or right eye detection from positional information on a fixation target, and may be performed.

It is transmitted to the image sensing light intensity setting unit 3 that the eye for image sensing is changed, and the image sensing light intensity setting unit 3 sets image sensing light intensity as follows (step S6).

(1) Setting of Value to which Predetermined Amount is Added

A value obtained by adding a predetermined amount stored in the image sensing light intensity setting unit 3 to the light intensity at the time of the last image sensing is set. This predetermined amount is a value which is what must be increased experientially since the eye to be examined becomes miosis by the last image sensing.

In addition, although it is mentioned as an example to store an absolute value of the predetermined amount to be increased here in the image sensing light intensity setting unit 3, it is not limited this. That is, it is also good to be so constituted as to store a rate on the basis of the light intensity at the time of the last image sensing. For example, in the case that "1.5" is stored, a value of F0×1.5 is set as the next image sensing light intensity from the last image sensing light intensity value F0.

(2) Setting by Pupil State of Eye to be Examined

Figure 3:
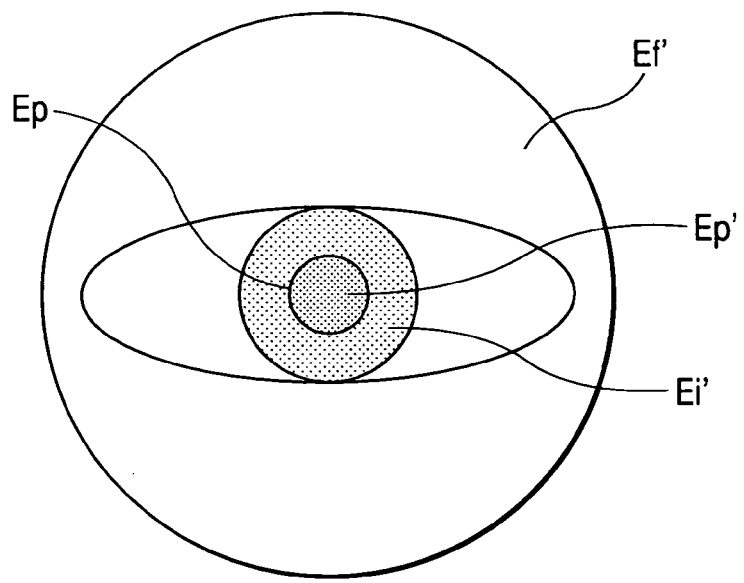
FIG. 3 being an explanatory diagram of an image of an anterior segment of eye.

A pupil region Ep' of the eye to be examined is extracted from an anterior segment image Ef of the eye to be examined, which is obtained by the observation CCD camera by illuminating the anterior segment of the eye to be examined with an anterior segment light source, and is shown in FIG. 3. Then, image sensing light intensity is set according to a region of the pupil region Ep'.

Figure 4:
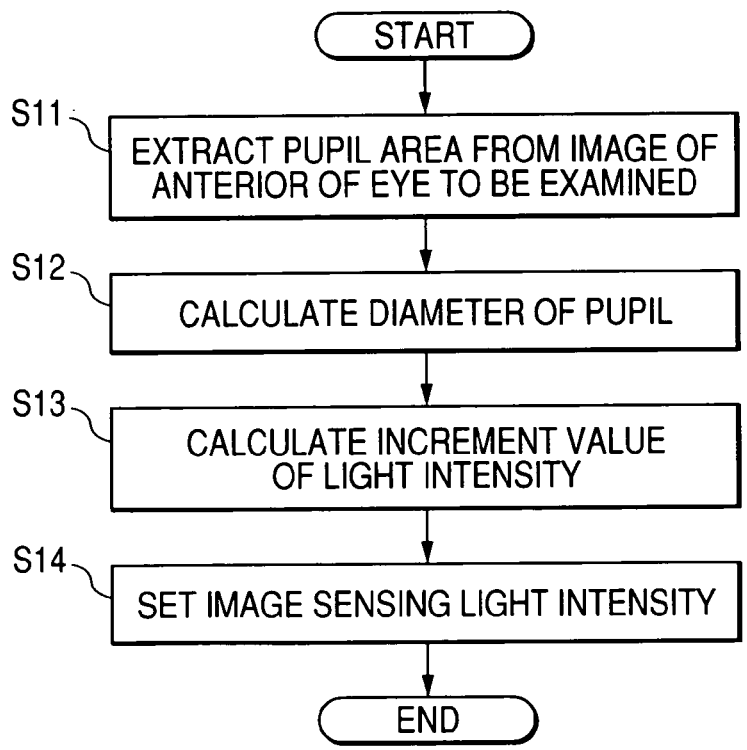
FIG. 4 being a flowchart at the time of setting image sensing light intensity according to a pupil state.

FIG. 4 is an operation flowchart for extracting the pupil region Ep' of the eye to be examined, which is shown in FIG. 3 (step S11). The extraction of the pupil region Ep' can be performed by known technology such as binarization processing using a suitable threshold from the luminance difference between an iris Ei and a pupil Ep.

Figure 5:
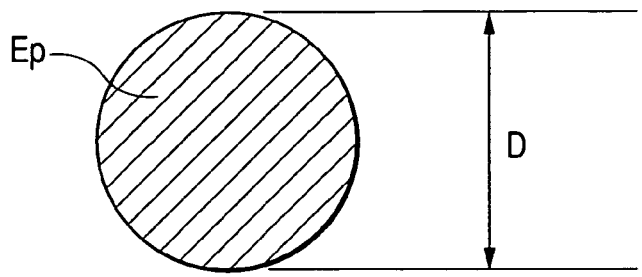
FIG. 5 being an explanatory diagram of a diameter of a pupil.

When the pupil region Ep' is extracted, a diameter D of the pupil is calculated as shown in FIG. 5 (step S12). This diameter D of the pupil is computable from a binary image having been used up to now.

An increment value of image sensing light intensity is calculated from the calculated diameter D of the pupil according to, for example, an increment-value-of-light-intensity conversion table of Table 1 which is stored in the image sensing light intensity setting unit 3 (step S13).

TABLE 1

| Diameter of pupil, D | Incremental value of image sensing light intensity |
|---|---|
| 2.5 mm | 0.8 |
| 3.0 mm | 0.6 |
| 3.5 mm | 0.4 |
| 4.0 mm | 0 |
| . | . |
| . | . |
| . | . |

Although an example that absolute values are listed in the table as increment values of image sensing light intensity to be added to the last image sensing light intensity value is shown in the example of Table 1, it is not limited to this. That is, it is also good to be so constituted as to list rates on the basis of the last image sensing light intensity similarly to the above-mentioned item [1].

When the incremental value of image sensing light intensity is calculated, a next image sensing light intensity value is calculated on the basis of the last image sensing light intensity value (step S14). Let the last image sensing light intensity value be F0, and when the diameter D of the pupil is 2.5 mm in an example of Table 1, F0+0.8 is set as the next image sensing light intensity value.

(3) Setting Based on Elapsed Time from Last Image Sensing

Although the pupil Ep of the eye to be examined was made miosis at the time of image sensing, when time elapses after the image sensing, the pupil Ep has opened gradually. Hence, it is necessary to set the image sensing light intensity at the time of the image sensing of another eye on the basis of the elapsed time until the image sensing of the other eye.

Table 2 shows an example of a correspondence table of incremental values of image sensing light intensity corresponding to the elapsed time from the last image sensing. This Table 2 shows the state that the incremental value of image sensing light intensity decreases with the elapsed time. For example, although F0+0.7 is set at the time of three minutes elapsing after the last image sensing, F0+0.3 is set after ten minutes elapses.

TABLE 2

| Elapsed time | Incremental value of image sensing light intensity |
|---|---|
| 1 min | 0.8 |
| 3 min | 0.7 |
| 5 min | 0.6 |
| 10 min | 0.3 |
| . | . |
| . | . |
| . | . |

The correspondence table is stored in the image sensing light intensity setting unit 3, and when image sensing light intensity is changed on the basis of elapsed time, it is referred to.

In addition, similarly to the case of item [2], it is also good to make not only the absolute value but also the rate based on the last image sensing light intensity the increment value of light intensity set in the table.

Although the operation of the image sensing light intensity setting unit 3 is explained with being divided into the above-mentioned items [1] to [3] in this embodiment, it is also possible to constitute the operation so as to set the image sensing light intensity by combining these cases.

When the light intensity setting at the time of another eye image sensing is completed, the another eye image sensing is performed similarly to step S1 to step S4 in the flowchart of FIG. 2 (steps S7 to S9). When the image sensing for a person to be examined is not completed (step S10), it returns to step S1.

Embodiment 2

Figure 6:
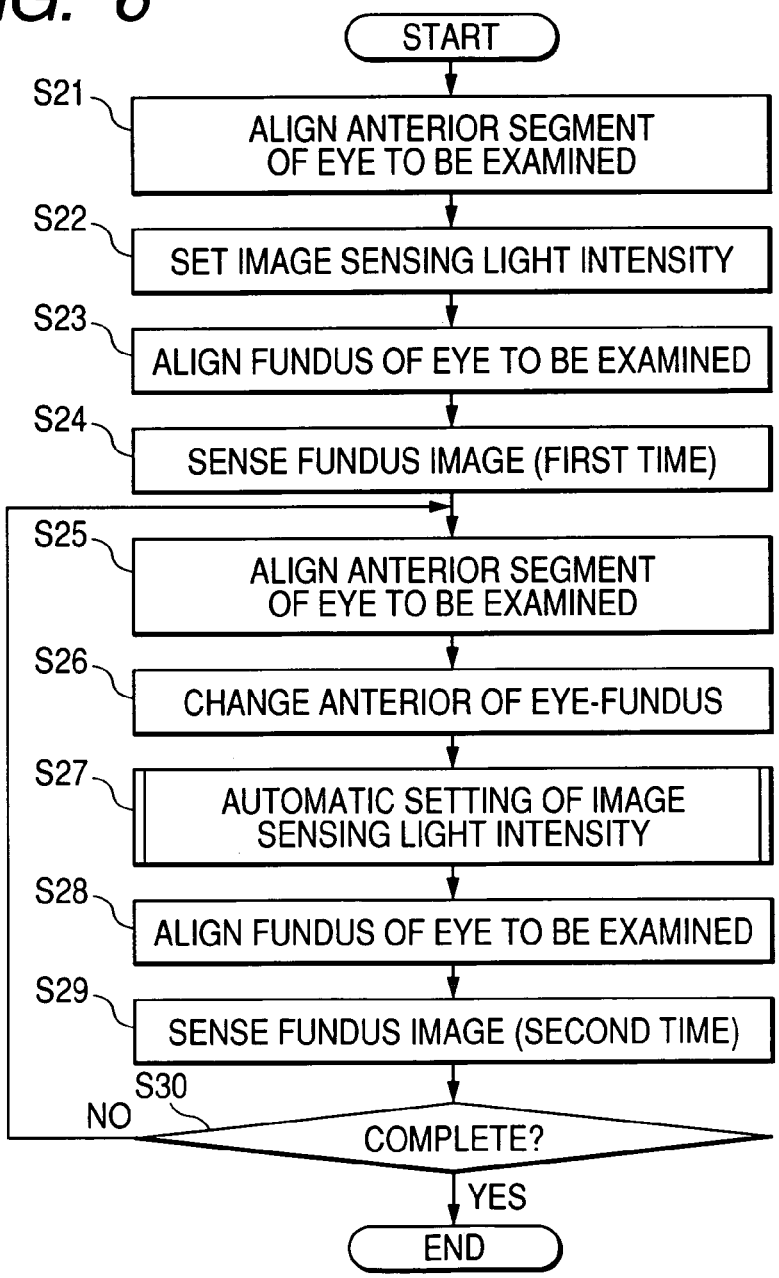
FIG. 6 being an operation flowchart of a second embodiment.

Although the case that images of right and left eyes are sensed continuously is mentioned as an example in the first embodiment, FIG. 6 is an operation flow chart of a second embodiment in the case of sensing images of the same eye to be examined continuously. Also in this second embodiment, the alignment of an anterior segment of eye (step S21), setting of image sensing light intensity (step S22), alignment of a fundus of eye (step S23), and fundus image sensing (step S24) are executed similarly to the case of the first embodiment.

At the second image sensing, after performing the alignment of an anterior segment of eye (step S25) first, next image sensing light intensity is set (step S27) with interlocking with the changing operation of the anterior/fundus examination changing switch (step S26) similarly to the first embodiment. A method of setting the image sensing light intensity here conforms to the method described in the first embodiment.

After the setting of image sensing light intensity, the alignment of a fundus of eye is performed in a fundus observing state into which the examination state is changed at step S26 (step S28), and fundus image sensing is executed (step S29). When the image sensing for a person to be examined is not completed (step S30), it returns to step S25. In addition, when the anterior/fundus examination changing operation is performed in order to return from the fundus observing state to the anterior observing state again, the image sensing light intensity set at step S27 is reset.

Furthermore, in the case of performing image sensing of the eye to be examined continuously, image sensing light intensity at the time of the next image sensing is automatically set with interlocking with the anterior/fundus examination changing operation.

In the above-mentioned description, although the case that the setting of image sensing light intensity is performed with interlocking with the anterior/fundus examination changing is mentioned as an example, it is not limited to this. That is, it is also good to be so constituted as to perform the setting by pushing the image sensing light intensity setting switch in the fundus camera 1 at the time of fundus examination.

Embodiment 3

Figure 7:
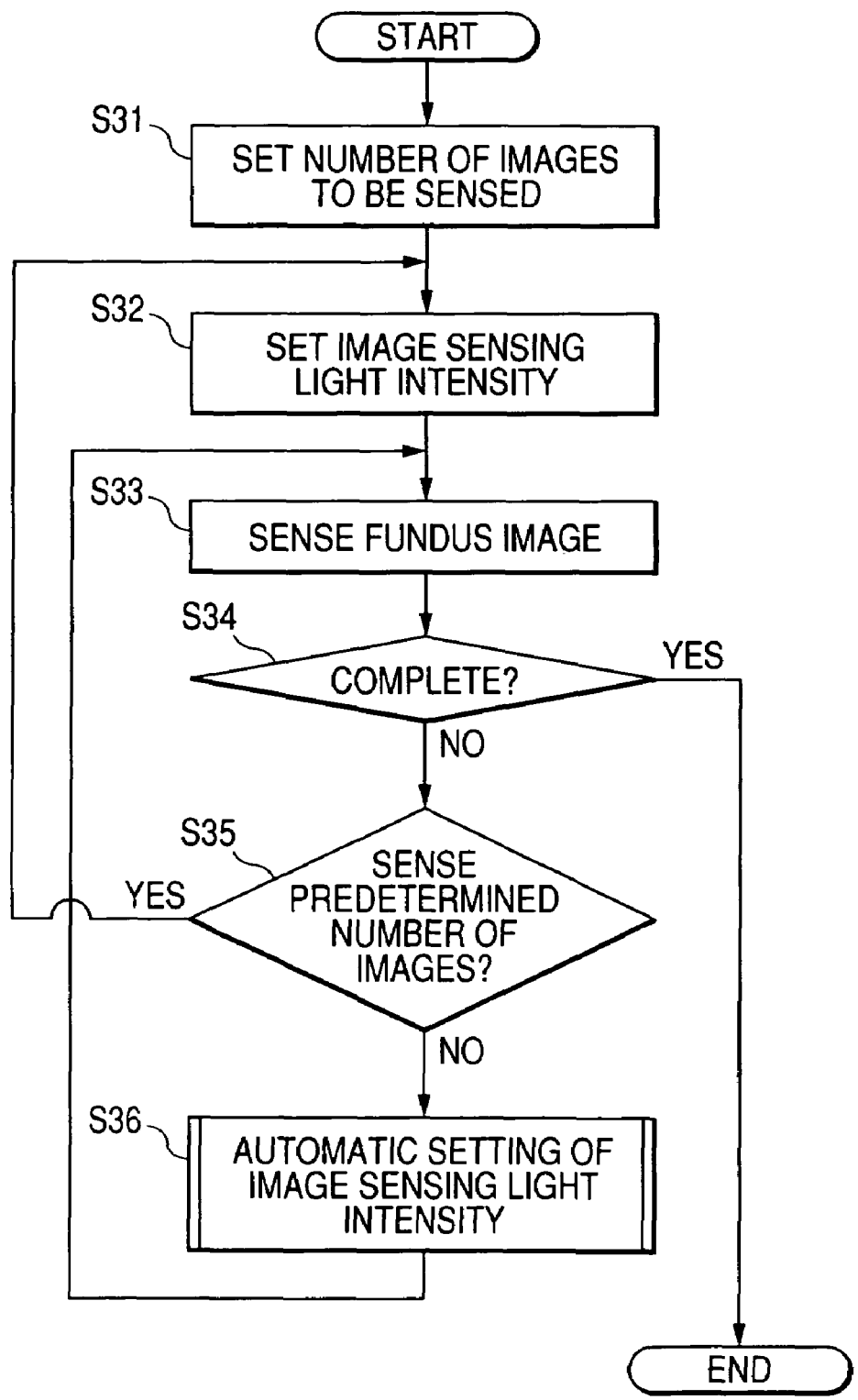
FIG. 7 being an operation flowchart of a third embodiment.

FIG. 7 is an operation flow chart in the case of setting the above-mentioned image sensing light intensity automatically within the limits of a predetermined image count in a third embodiment. In a mass health examination and a complete physical examination, there is a case of performing various types of image sensing for the same eye to be examined, such as wide angle image sensing, and narrow angle image sensing with optically enlarging a characteristic region. In this case, since a number of images every eye to be examined is generally the same, the number of images of the same eye to be examined is beforehand registered into the image sensing light intensity setting unit 3 by a number of images setting unit, which is not shown (Step S31).

When sensing images, the first setting of image sensing light intensity is performed (step S32) similarly to the above-mentioned other embodiments. After the setting of image sensing light intensity is completed and the alignment of an anterior segment of eye and a fundus of eye, and the like are performed, images of the eye to be examined are sensed (step S33).

In addition, in the flowchart of FIG. 7, since the alignment of an anterior segment of eye and a fundus of eye is equivalent to those of the above-mentioned other embodiments, its description is omitted. In the case of continuing image sensing after the completion of the first image sensing (step S34), it is performed to compare a count of images, which have been already sensed, with the number of images set at step S31 (step S35). When it reaches the number of images set at step S31, it changes to step S32 and image sensing light intensity is set again (step S36). Furthermore, here, although the image sensing light intensity is set again when it reaches the number of images set, it is not limited to this. Namely, the image sensing light intensity may be reset to a predetermined value.

On the other hand, when the number of images set is not reached, the image sensing light intensity at the time of the next image sensing is set automatically on the basis of the same algorithm as that in the case of other embodiments (step S36). When the image sensing light intensity at the time of the next image sensing is determined, fundus image sensing is executed at step S33.

Embodiment 4

Figure 8:
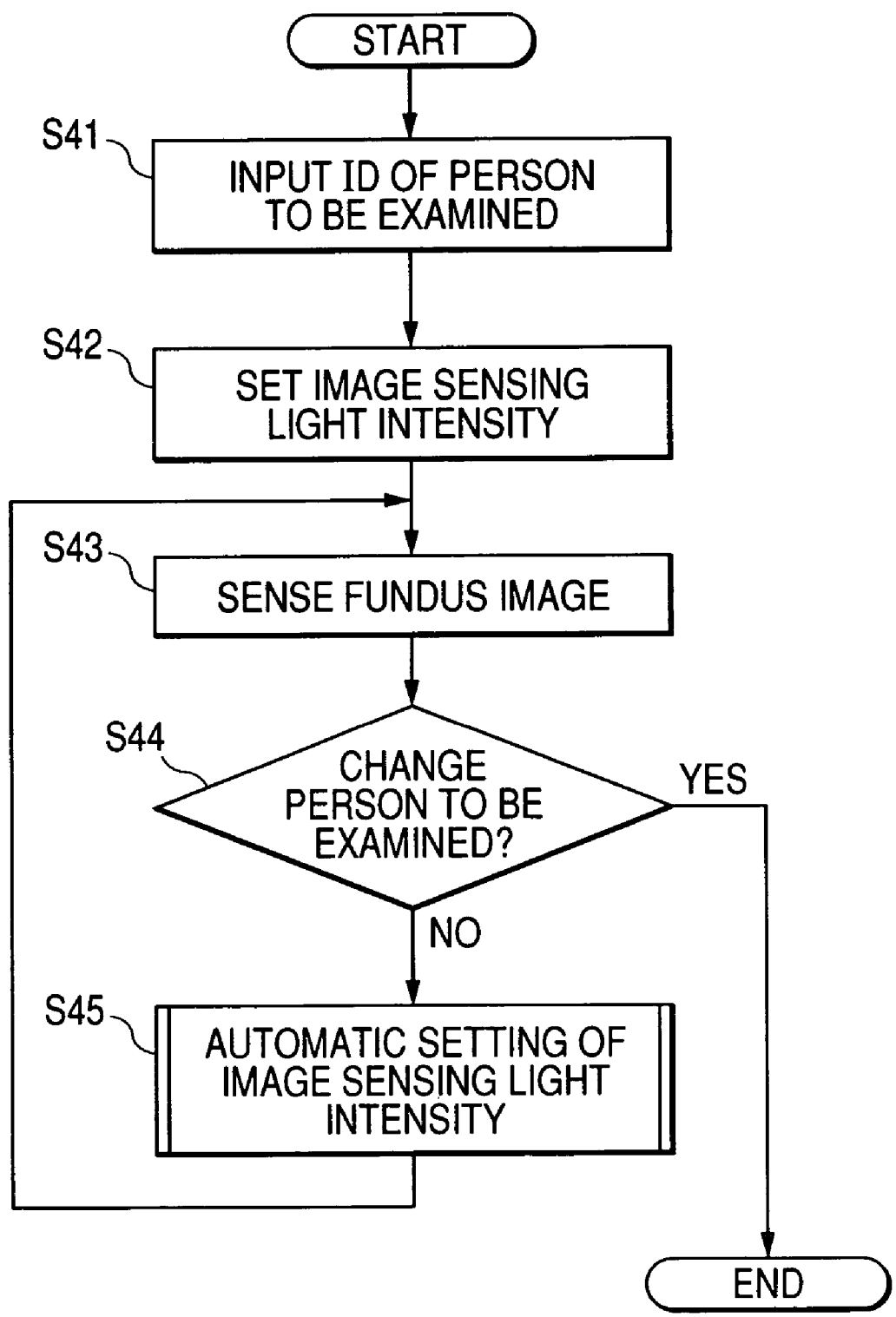
FIG. 8 being an operation flowchart of a fourth embodiment.

FIG. 8 is an operation flow chart in the case of setting the next image sensing light intensity automatically until a person to be examined is changed in a fourth embodiment. Although the image sensing light intensity at the time of the next image sensing is set automatically according to a number of images set beforehand in the third embodiment, a limit of automatic setting is made to be the change of an ID of a person to be examined in this fourth embodiment.

First, an ID (identifier) of a person to be examined whose image will be sensed from now on is inputted from an input unit of an ID of a person to be examined in the fundus camera 1 (step S41). When the setting of the ID of the person to be examined is completed, the image sensing light intensity setting (step S42), and fundus image sensing (step S43) are performed similarly to the third embodiment.

In the case that a person to be examined is changed and image sensing is continued (step S44), an ID of a person to be examined, which is sensed next, is inputted at step S41. After reinputting the ID of the person to be examined, the image sensing light intensity at the time of the next image sensing is set. In addition, although image sensing light intensity is set similarly to the case that the ID of the person to be examined is inputted first also when the ID of the person to be examined is reinputted here, it is not limited to this. That is, it is also good to be so constituted as to reset the image sensing light intensity to a predetermined value.

When images of the same person to be examined are sensed continuously, the image sensing light intensity at the time of the next image sensing is set automatically on the basis of the same algorithm as that in the case of other embodiments (step S45).

Embodiment 5

Figure 9:
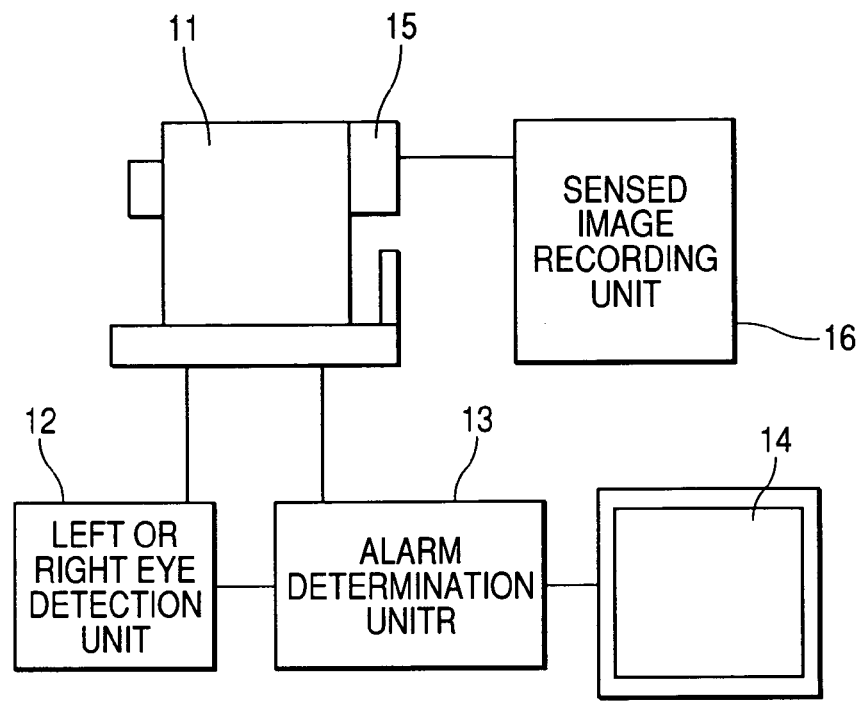
FIG. 9 being a structural diagram of an apparatus of a fifth embodiment.

What are mentioned as examples in the first embodiment are cases of setting the image sensing light intensity at the time of the next image sensing with increasing the image sensing light intensity by a predetermined amount from the light intensity at the time of the last image sensing and with interlocking with right and left eye changing, according to the algorithms in items [1] to [3]. FIG. 9 is an apparatus structural diagram of a fifth embodiment where an alarm which prompts the change of light intensity from the last image sensing light intensity is issued.

A left or right eye detection unit 12 and an alarm determination unit 13 are connected to a fundus camera 11, and a monitor 14 is connected to the alarm determination unit 13. In addition, an output of a CCD camera 15 is connected to a sensed image recording unit 16.

First fundus image sensing is performed with conforming to the first embodiment, and right and left eyes are changed so as to sense an image of another eye after the completion of image sensing. It is transferred from the left or right eye detection unit 12 to the alarm determination unit 13 that the right and left eyes are changed, and the alarm determination unit 13 performs alarm display on the monitor 14 according to the following algorithm.

(1) Alarm after Right and Left Eye Changing

When the first image sensing is completed and the right and left eyes are changed, the alarm display is performed on the monitor 14.

(2) Alarm by Pupil State of Eye to be Examined

Figure 10:
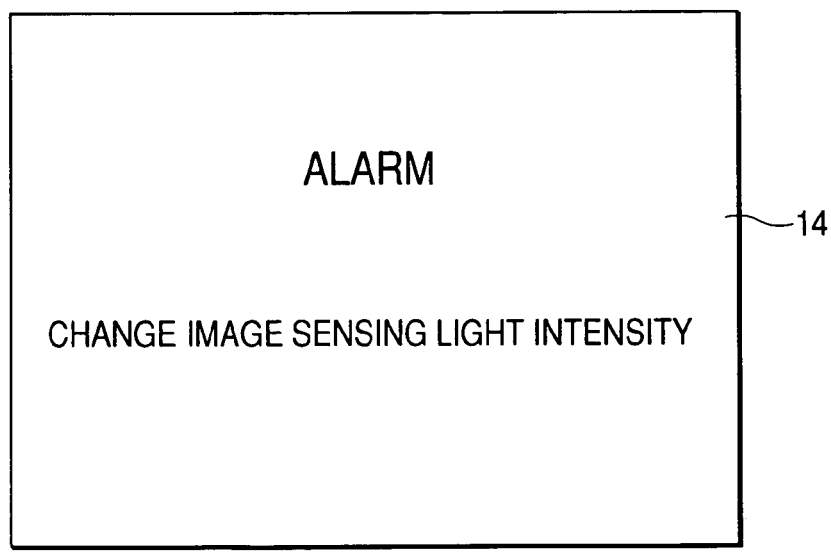
FIG. 10 being an explanatory diagram of an alarm display screen.

A measured value of a diameter of a pupil of the eye to be examined is compared using a determination threshold of a diameter of a pupil stored beforehand in the alarm determination unit 13. When being not larger than the determination threshold, for example, the alarm display is performed on the monitor 14 as shown in FIG. 10. The determination threshold is an experience value of the diameter of a pupil considered to need the change of image sensing light intensity.

In addition, although the case that an alarm is determined by comparing a diameter of a pupil here is mentioned as an example and described, it is not limited to this. It is also possible to be so constituted as to perform determination with an area value of a pupil region.

(3) Alarm Based on Elapsed Time from Last Image Sensing

A measured elapsed time is compared using a determination threshold of the elapsed time from the last image sensing stored beforehand in the alarm determination unit 13. When being not larger than the determination threshold, the alarm display is performed similarly to the above-described items [1] and [2]. The determination threshold is an experience value of the elapsed time considered to need the change of image sensing light intensity.

In addition, although the alarm is made the alarm display on the monitor 14 in the above-mentioned description, it is not limited to this. But, it is also good to be a beep such as a buzzer. In addition, also in the fourth embodiment, it is also good to be so constituted as to issue an alarm on the basis of an alarm determination as shown in the fifth embodiment.

According to the above embodiments, it is possible to sense images of an eye to be examined in proper image sensing light intensity without performing the troublesome operation of adjusting image sensing light intensity manually every image sensing when performing continuous image sensing for the same person to be examined.

The present invention will be described in detail on the basis of embodiments shown.

Embodiment 6

Figure 11:
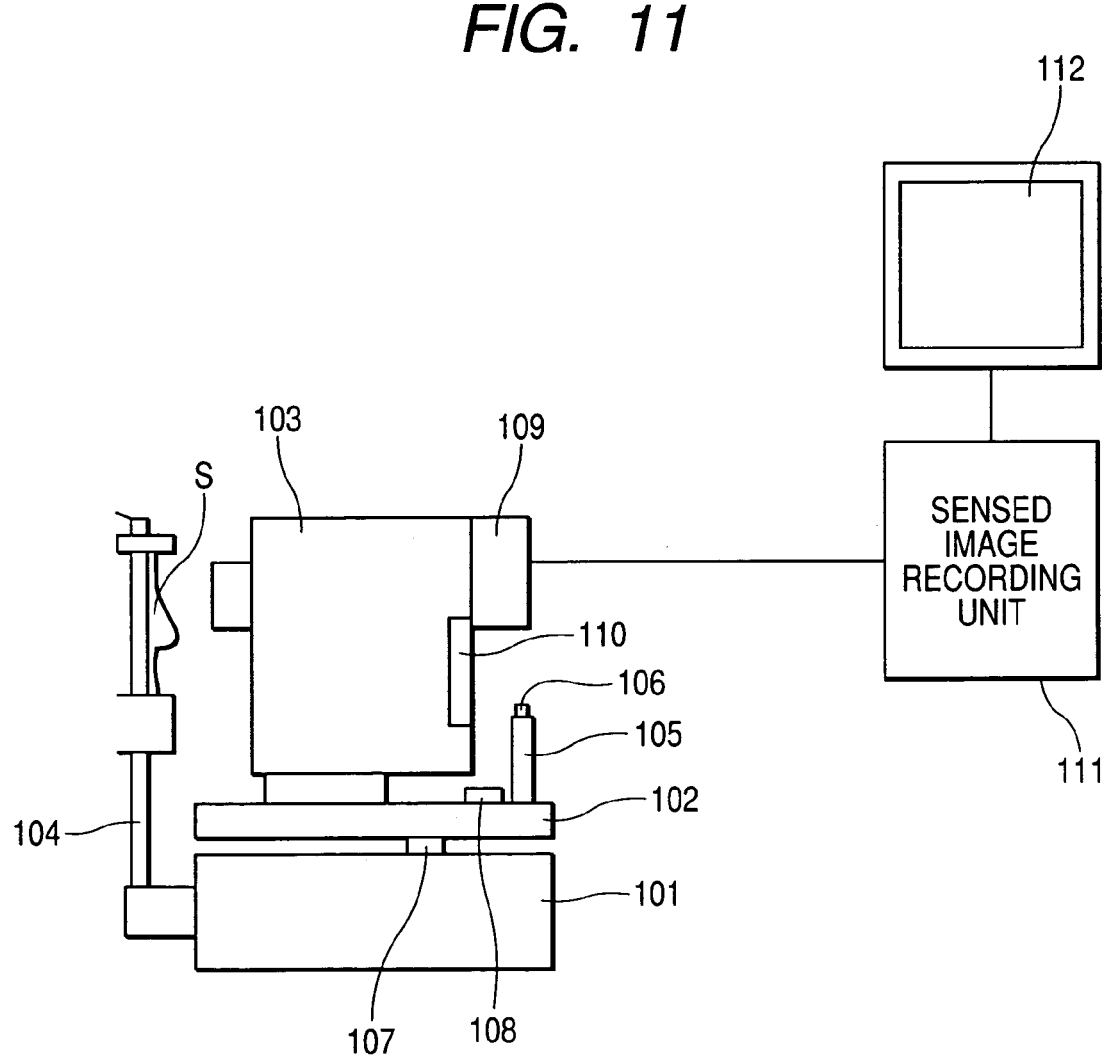
FIG. 11 being a structural diagram of an apparatus of an embodiment.

FIG. 11 shows an apparatus structural diagram of another embodiment of the present invention. A stage unit 102 is laid on a base unit 101, and a fundus camera 103 is provided on it. The face rest 104 is installed on the base unit 101, and a jaw and a forehead of a person S to be examined are contacted to the face rest 104 to fix an eye E to be examined. A camera person can move the fundus camera 103 back and forth, and right and left to the person S to be examined by operating an operation rod 105 on the stage unit 102. In addition, a sensing switch 106 is provided on the operation rod 105.

On the base unit 101, a right or left detection unit 107 which detects a moving direction of the stage unit 102 is provided, and an image sensing light intensity setting unit 108 is provided on the stage unit 102. In addition, a CCD camera 109 and an observing-monitor 110 are provided in the fundus camera 103, and an output of the CCD camera 109 is connected to a sensed image recording unit 111 and a TV monitor 112.

Figure 12:
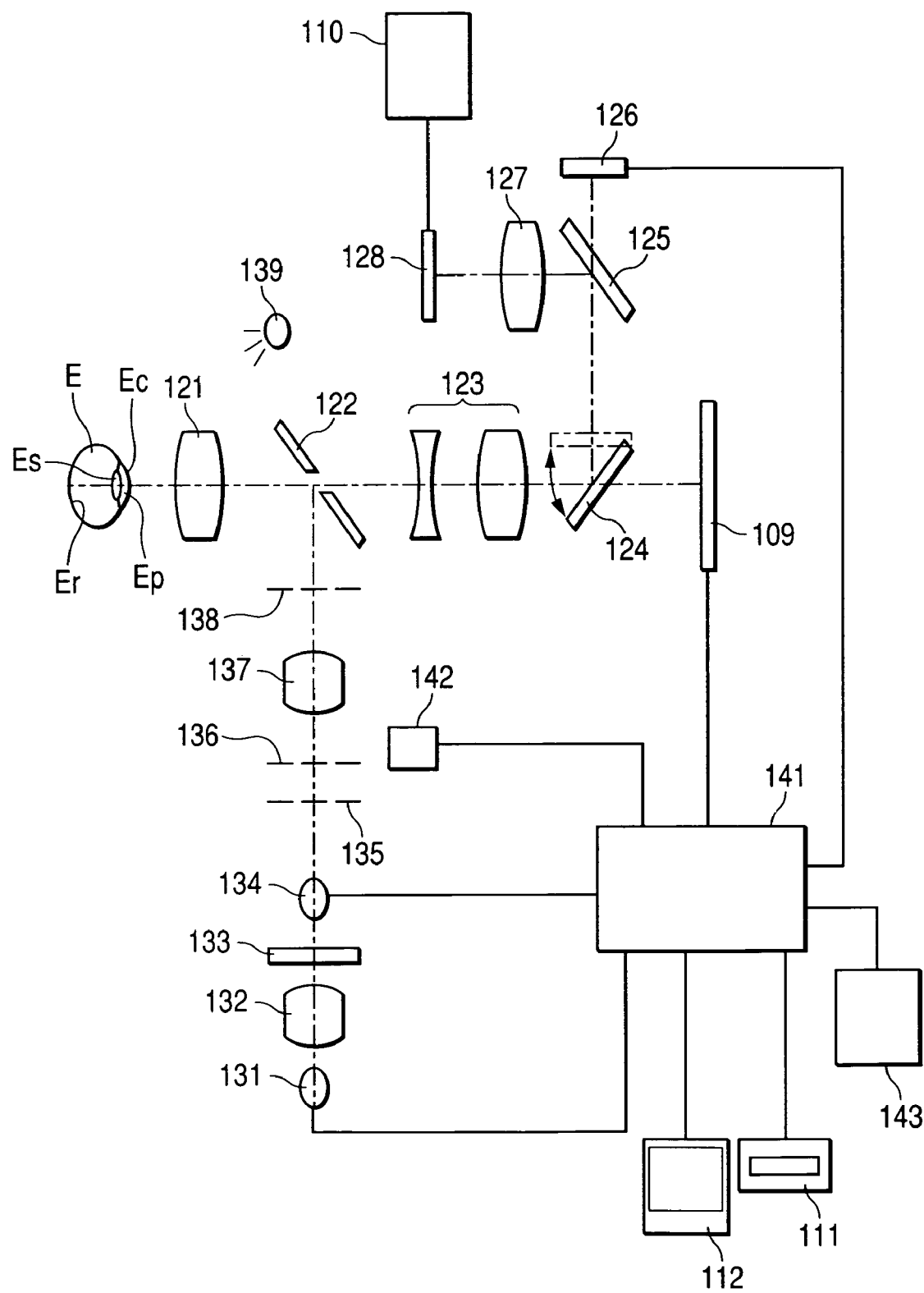
FIG. 12 being a structural diagram of a fundus camera.

FIG. 12 shows a structural diagram of the fundus camera 103. An objective lens 121 is arranged in front of the eye E to be examined. On an optical path behind it, a perforated mirror 122, an image sensing lens 123 movable for focus adjustment, a movable mirror 124, and the CCD camera 109 which has sensitivity in a visible wavelength region are arranged sequentially, which constitute a fundus image sensing optical system.

In a reflecting direction of the movable mirror 124, a half-mirror 125 and a fixation lamp 126 which is in an approximately conjugate position with a fundus Er of eye are arranged. In a reflecting direction of the half-mirror 125, a field lens 127, and an observing camera 128 which has sensitivity in an infrared wavelength region are arranged sequentially. An output of the observing camera 128 is connected to the observing monitor 110, which constitute an observation optical system.

In addition, an illumination optical system is provided in an incident direction of illumination light to the perforated mirror 122. In view of an observing light source 131, which emits visible light, such as a halogen lamp, a condenser lens 132, a visible light cut-off filter 133, a sensing light source 134 which emits the flash of visible light, a ring slit 135 which has a ring-shaped opening and is in an approximate conjugate position with the pupil Ep of the eye E to be examined, a crystalline lens baffle 136 which has a ring-shaped opening and is in an approximate conjugate position with a rear surface of a crystalline lens Es of the eye E to be examined, a lens 137, and a cornea baffle 138 which has a ring-shaped opening and is in an approximate conjugate position with the cornea Ec of the eye to be examined are arranged sequentially. In addition, an observing light source 139 for an anterior segment of eye is provided in front of the eye E to be examined.

An output of the CCD camera 109 is connected to control means 141 which consists of a CPU. What are connected to the control means 141 are the fixation lamp 126, observing light source 131, sensing light source 134, TV monitor 112, detection means 142, such as a micro switch which detects a state of the crystalline lens baffle 136, the sensed image recording unit 111, main memory 143 which functions as working memory while storing a program required for processing in the control means 141, various kinds of data, and the like.

Figure 13:
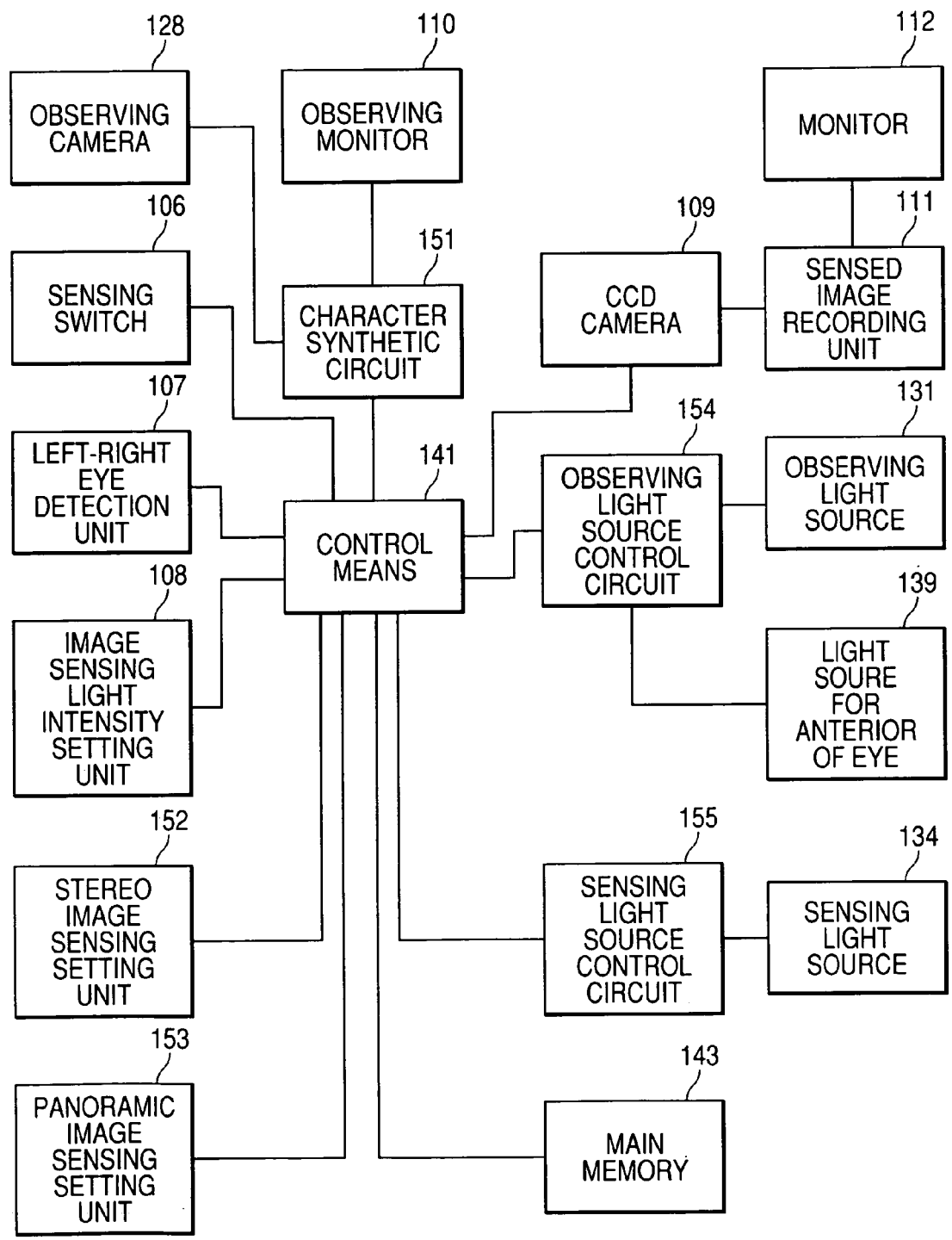
FIG. 13 being a block diagram of circuits.

FIG. 13 is a block circuit structural diagram, and the same reference numerals as those in FIGS. 11 and 12 show the same members respectively. The control means 141 performs the processing of the entire fundus camera 103 according to the program written in the main memory 143. The observing camera 128 senses images of the anterior segment and fundus Er of the eye E to be examined. Characters, marks, and the like, such as an alignment mark, characters showing directions of right and left eyes, and a value showing image sensing light intensity are synthesized electrically with the video signal in a character synthetic circuit 151 to be displayed on the observing monitor 110. The control means 141 designates the characters to be synthesized. The sensing switch 106, a stereo image sensing setting unit 152, and a panoramic image sensing setting unit 153 are connected to the control means 141. Furthermore, the observing light source 131 for an fundus of eye is controlled by the observing light source control circuit 154 connected to the control means 141, and the sensing light source 134 is controlled by the sensing light source control circuit 155.

The determination of right and left eyes is performed by the left or right eye detection unit 107 which detects whether the stage unit 102 moves in any direction of the right and left to the base unit 101. In addition, the determination is used in order to sense an image by moving the fundus camera 103 up and down by rotating the operation rod 105, and performing the alignment adjustment of an optical axis of the fundus camera 103 with the eye E to be examined with displaying the anterior segment of the eye E to be examined by the observing camera 128 on the observing monitor 110, and working distance adjustment and focus adjustment with displaying the fundus Er of eye. When displaying an anterior segment of eye, an observing lens for an anterior segment of eye is inserted into the optical axis in the fundus camera 103, the anterior segment of eye is illuminated by the observing light source 139 for an anterior segment of eye, and an iris of the eye E to be examined and the pupil Ep are enlargingly displayed on the observing monitor 110.

Figure 14:
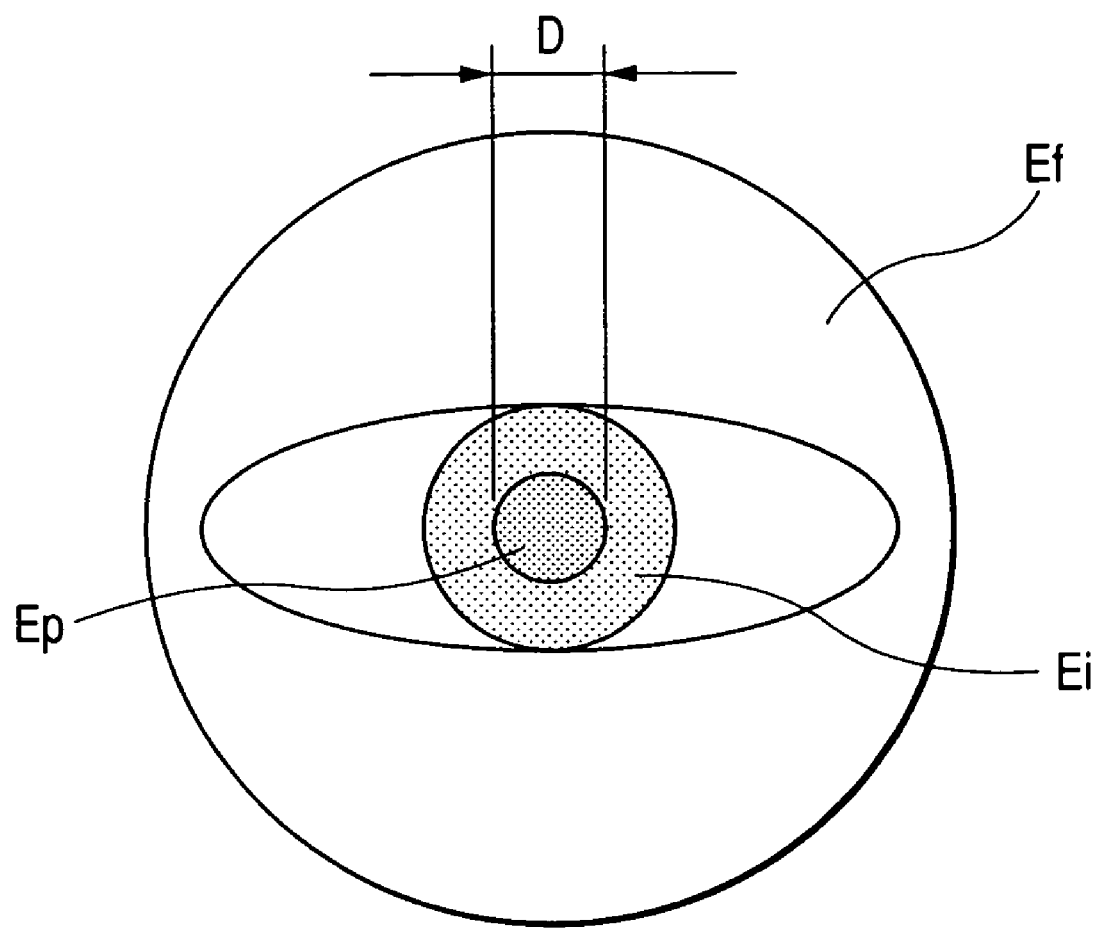
FIG. 14 being an example of an image of an anterior segment of eye and a diameter of a pupil.

FIG. 14 shows an aspect of observing the anterior segment Ef of eye. When observing the fundus Er of eye, the observing lens for an anterior segment of eye is departs from the optical axis, and a fundus image is displayed on the observing monitor 110. It is possible to change the observing lens for an anterior segment of eye by a switch arranged in the stage unit 102. In addition, at the time of observing an anterior segment of eye and a fundus of eye, they are illuminated with the near-infrared light source by which the eye E to be examined does not become miosis, and the observing camera 128 has sensitivity in the infrared region.

The fundus image sensed by the CCD camera 109 using visible light is recorded by the sensed image recording unit 111, and is displayed on the TV monitor 112.

Figure 15:
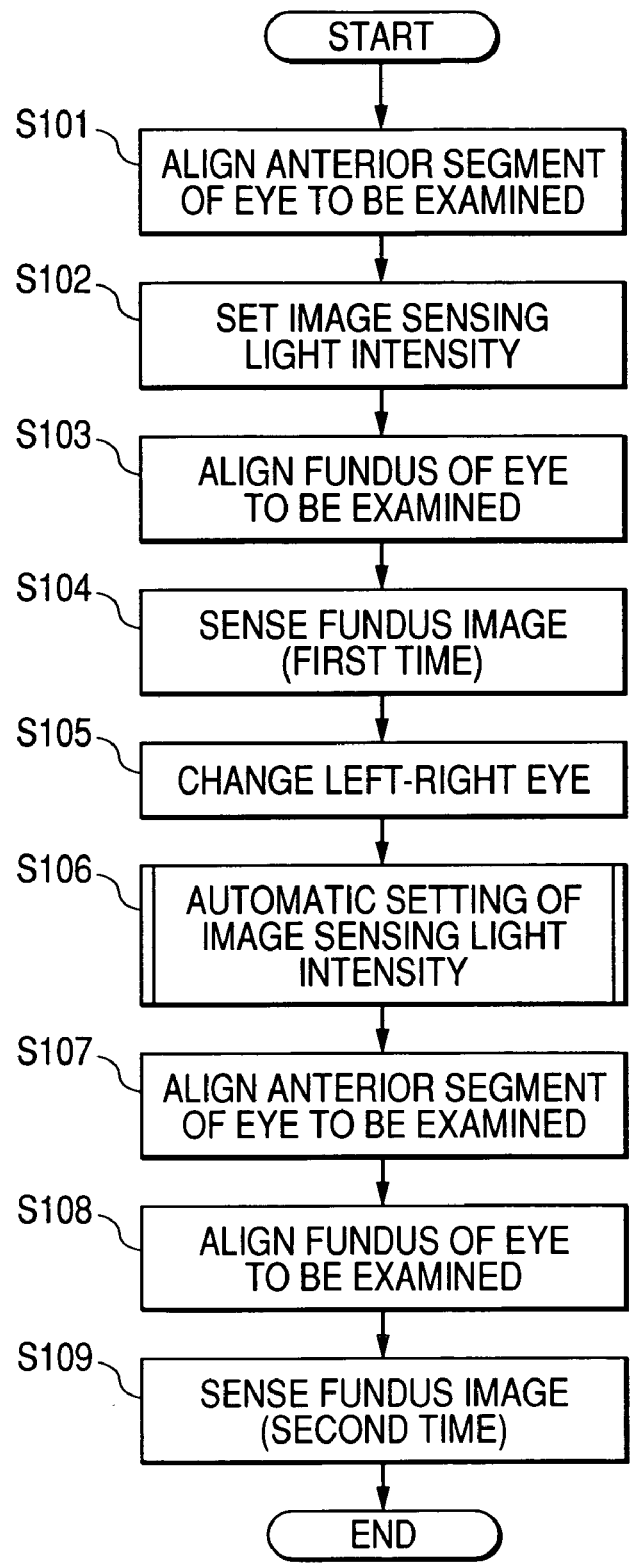
FIG. 15 being an operation flowchart of a sixth embodiment.

FIG. 15 is a flowchart of an execution procedure in the case of performing fundus image sensing of right and left eyes in a sixth embodiment.

(Step S101) The person S to be examined is replaced, and a light intensity correction value is reset. The alignment of an anterior segment of eye of a right eye (or left eye) of the person S to be examined with the optical axis of the fundus camera 103 is performed.

(Step S102) When the alignment of the anterior segment of eye is completed, image sensing light intensity is set. Since natural mydriasis is enough performed under a darkroom environment before the first image sensing is performed, the fine adjustment of image sensing light intensity every person S to be examined is unnecessary. But, when a mydriasis state is inadequate especially, image sensing light intensity is set arbitrarily.

(Step S103) It is changed to a fundus examination from an anterior observing state, and alignment with the fundus Er of eye is performed.

(Step S104) After the alignment is completed, the sensing light source 134 emits light and an image of the fundus Er of eye is sensed by pushing the sensing switch 106 in the upper portion of the operation rod 105. The fundus image sensed by the CCD camera 109 is recorded and saved by the sensed image recording unit 111, and is displayed on the TV monitor 112, and the image sensing of the right eye (or left eye) is completed.

(Step S105) The stage unit 102 is moved in a direction of a left eye (or right eye). The left or right eye detection unit 107 detects that an eye for image sensing changes with the move of the stage unit 102.

(Step S106) The change of the eye E to be examined is inputted into the image sensing light intensity setting unit 108, and the next image sensing light intensity is set.

(Step S107) The alignment of an anterior segment of eye of a left eye (or right eye) with the optical axis of the fundus camera 103 is performed.

(Step S108) It is changed to a fundus examination from an anterior observing state, and alignment with the fundus Er of eye is performed.

(Step S109) After the alignment is completed, the sensing switch 106 is pushed and the image of the fundus Er of eye of the left eye (or right eye) is sensed. The fundus image sensed by the CCD camera 109 is recorded and saved by the sensed image recording unit 111, and is displayed on the TV monitor 112.

Although the image sensing light intensity is changed at the above-described step S106, the light intensity change is made by any of the following three patterns.

Image Sensing Light Intensity Change 1

The next image sensing light intensity is defined to be a predetermined amount based on the last image sensing light intensity.

Light intensity is set from a table or the like at the time of first image sensing, and the image sensing light intensity at and after the next image sensing is determined. This predetermined amount is a value stored in the image sensing light intensity setting unit 108, and this value is a value which must be increased experientially since the eye E to be examined becomes miosis in the last image sensing.

Table 1 is an example of storing absolute values of the increasing predetermined amount as a table. For example, when the light intensity at the time of the last image sensing was "F0", as the next image sensing light intensity, a value in the left column and "F0" row in Table 1 is called, and the light intensity of "F1" is set as the next image sensing light intensity.

TABLE 1

| Incremental value of image sensing light intensity | | |
|---|---|---|
| A | B | |
| F0 | F1 | F1- |
| F1 | F2 | F2- |
| F2 | F3 | F3- |
| F3 | F4 | F4- |
| . | | |
| . | | |
| . | | |

Here, although illustration is omitted, it is also possible to change and use columns A and B by setting. For example, it is also possible to use column A for the same eye, and to use column B for the other eye. In addition, although it is mentioned as an example to store an absolute value of the predetermined amount to be increased here in the image sensing light intensity setting unit 108, it is not limited this. That is, it is also good to adopt the constitution of storing a rate on the basis of the light intensity at the time of the last image sensing. For example, in the case that "1.5" is stored, a value of F0×1.5 is set as the next image sensing light intensity from the last image sensing light intensity value F0.

Table 2 is an example of a table storing a magnification to the last image sensing light intensity instead of an absolute value as the correction value.

TABLE 2

| Incremental value of image sensing light intensity | |
|---|---|
| A | B |
| F0 | 1.50 | 1.40 |
| F1 | 1.51 | 1.41 |
| F2 | 1.52 | 1.42 |
| F3 | 1.53 | 1.43 |
| . | | |
| . | | |
| . | | |

When an image is sensed at "F0", a value in column A or B of row "F1" in the left column is read. When the column A is used, the next image sensing light intensity is set as "F0× 1.50".

Image Sensing Light Intensity Change 2

The next image sensing light intensity is made to be a value obtained by adding a function (a diameter of a pupil or an area of a pupil region) to the last image sensing light intensity.

Figure 16:
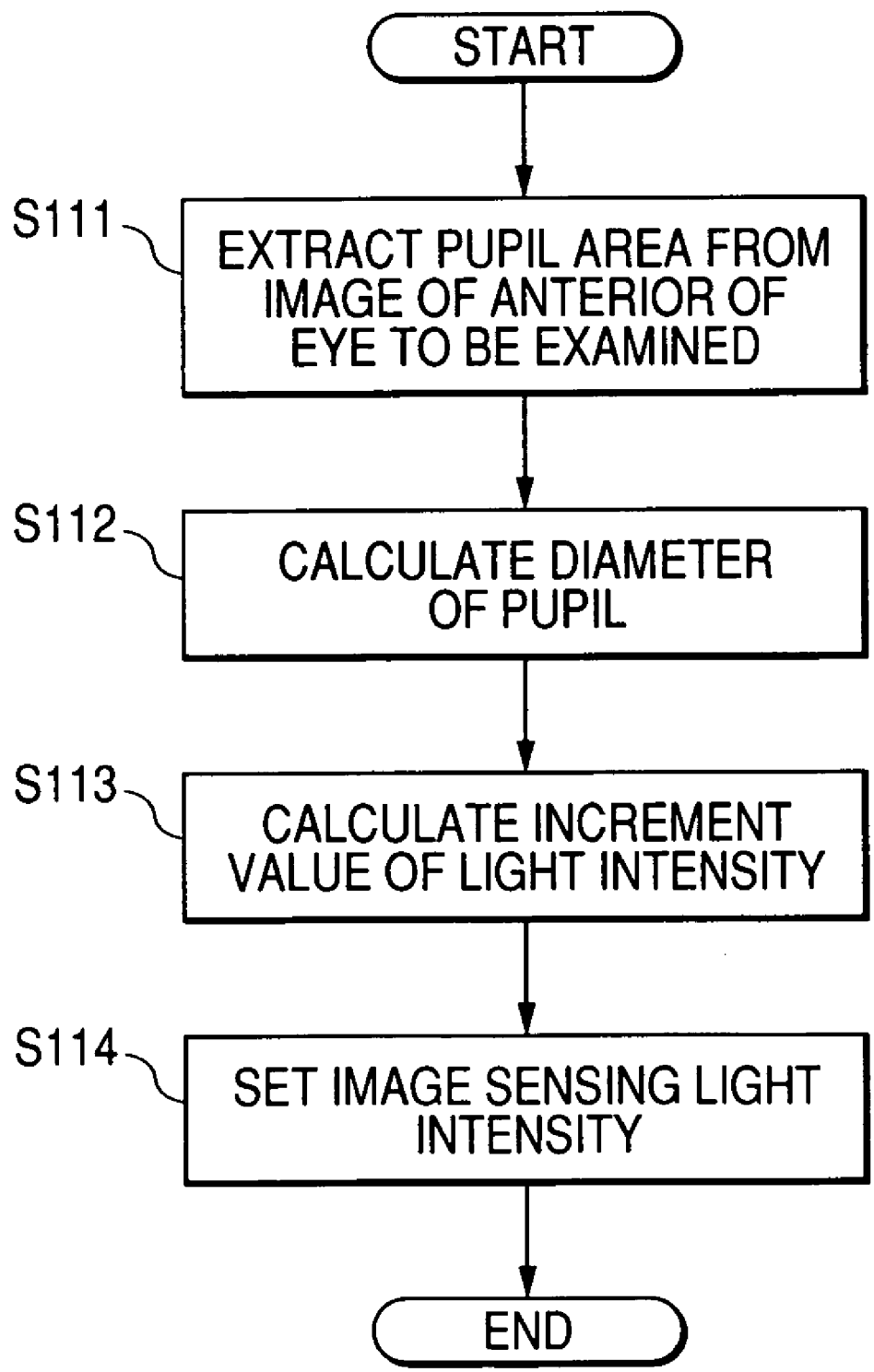
FIG. 16 being an operation flowchart at the time of changing image sensing light intensity according to a diameter of a pupil.

A region of the pupil Ep is extracted from an image of the anterior segment of the eye to be examined and to be shown in FIG. 14, and this function is set as a next image sensing light intensity correction value according to the area of this region. FIG. 16 is an operation flowchart for deducing a correction value of the next image sensing light intensity from the diameter of the pupil.

(Step S111) Binarization processing is first performed using a suitable threshold from luminance difference between the iris Ei and pupil Ep from the anterior segment image shown in FIG. 14, and the pupil region is extracted. Since the anterior segment image is illuminated by the infrared light source, the iris Ei and pupil Ep are easily separable.

(Step S112) The diameter D of the pupil is calculated from the separated pupil region. This diameter D of the pupil is computable from the binary image by a calculating method having been used up to now.

(Step S113) An increment value of image sensing light intensity is calculated from an increment-value-of-light-intensity conversion table shown in Table 3 which is stored in the image sensing light intensity setting unit 108 on the basis of the diameter D of the pupil.

TABLE 3

| Diameter of pupil, D | Incremental value of image sensing light intensity |
|---|---|
| 2.5 mm | 0.8 |
| 3.0 mm | 0.6 |
| 3.5 mm | 0.4 |
| 4.0 mm | 0.3 |
| . | . |
| . | . |
| . | . |

Although values of this increment-value-of-light-intensity conversion table are absolute values of increment values of image sensing light intensity to be added to the last image sensing light intensity value, it is not limited to this. That is, it is also good to adopt the constitution of listing rates on the basis of the last image sensing light intensity.

(Step S114) When the incremental value of image sensing light intensity is calculated, a next image sensing light intensity value is calculated by adding the incremental value to the last image sensing light intensity value. In this example, let the last image sensing light intensity value be F0, and when the diameter D of the pupil is 2.5 mm, F0+0.8 is set as the next image sensing light intensity value.

Image Sensing Light Intensity Change 3

The next image sensing light intensity is made to be a value obtained by adding a function (elapsed time) to the last image sensing light intensity.

Although the pupil Ep of eye was made miosis at the time of image sensing, as time lapses after the image sensing, the pupil Ep has opened gradually. Hence, it is also good to correct the image sensing light intensity at the time of the image sensing of another eye on the basis of the elapsed time until the image sensing of the other eye. Thus, the next image sensing light intensity is obtained by adding the correction value, based on the function of an elapsed time, to the last image sensing light intensity. A correspondence table in Table 4 lists values calculated by this function.

TABLE 4

| Elapsed time | Incremental value of image sensing light intensity |
|---|---|
| 1 min | 0.8 |
| 3 min | 0.7 |
| 5 min | 0.6 |
| 10 min | 0.3 |
| . | . |
| . | . |
| . | . |

This correspondence table shows incremental values of image sensing light intensity corresponding to the elapsed time from the last image sensing. In this example, the incremental value of image sensing light intensity decreases with the elapsed time. For example, although F0+0.7 is set at the time of three minutes elapsing after the last image sensing, F0+0.3 is set after ten minutes elapses. The correspondence table is stored in the image sensing light intensity setting unit 108, and when image sensing light intensity is changed on the basis of an elapsed time, it is referred to. It is also good to make not only the absolute value but also the rate based on the last image sensing light intensity the value in this correspondence table.

Embodiment 7

Figure 17:
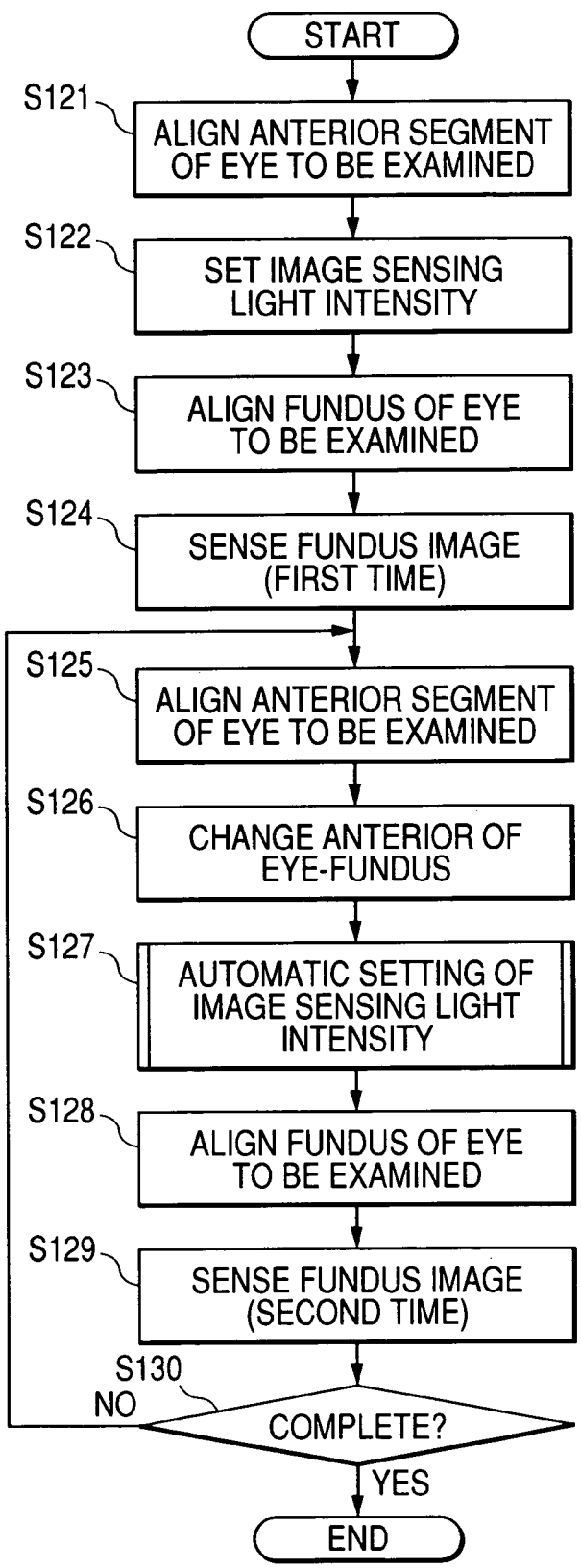
FIG. 17 being an operation flowchart of a seventh embodiment.

Although the case that images of right and left eyes are sensed continuously is mentioned as an example in the sixth embodiment, FIG. 17 is an operation flow chart in the case of sensing images of the same eye E to be examined continuously.

(Step S121) The fundus camera 103 is in an anterior segment observing state, and resets the correction value of light intensity. The alignment of an anterior segment of eye of a right eye (or left eye) of the person S to be examined with the optical axis of the fundus camera 103 is performed.

(Step S122) Image sensing light intensity is set.

(Step S123) It is changed to an observing state of the fundus Er of eye, and alignment with the fundus Er of eye is performed.

(Step S124) The sensing switch 106 is pushed and first fundus image sensing is performed. After the image sensing, it is changed to an anterior segment observing state. The fundus image sensed by the CCD camera 109 is recorded and saved by the sensed image recording unit 111, and is displayed on the TV monitor 112.

(Step S125) It is changed to a left eye (or right eye), or the alignment of the anterior segment of eye is performed for the same eye.

(Step S126) After the alignment of the eye E to be examined with the optical axis is completed, it is changed to a fundus observing state.

(Step S127) The change to the fundus observing state is inputted into the image sensing light intensity setting unit 108, and the next image sensing light intensity is changed. Since it is changed to the fundus observing state from the anterior observing state after the first image sensing, the next image sensing light intensity is corrected.

(Step S128) Working distance adjustment and focus adjustment on the fundus Er of eye are performed.

(Step S129) The sensing switch 106 is pushed and second fundus image sensing is performed. The fundus image sensed by the CCD camera 109 is recorded and saved by the sensed image recording unit 111, and is displayed on the TV monitor 112. An observing state of the fundus camera 103 is changed to the anterior segment observing state. Here, when the image sensing of this person S to be examined is completed, or is performed repeatedly, it returns to step S125.

As to a next image sensing light intensity setting method performed at the above-described step S127, any one of the three changing methods described in the first embodiment is applied.

Furthermore, in the case of the same eye in the image sensing of changing right and left eyes, it is also possible to change a changing amount by the three changing methods in the first embodiment. In this case, it is also conceivable to multiply a changing amount by a coefficient, such as 0.9, in the right and left eye change.

In addition, it is possible to suppress the variance of an opening degree of the pupil Ep between right and left eyes by changing the image sensing light intensity.

Embodiment 8

Figure 18:
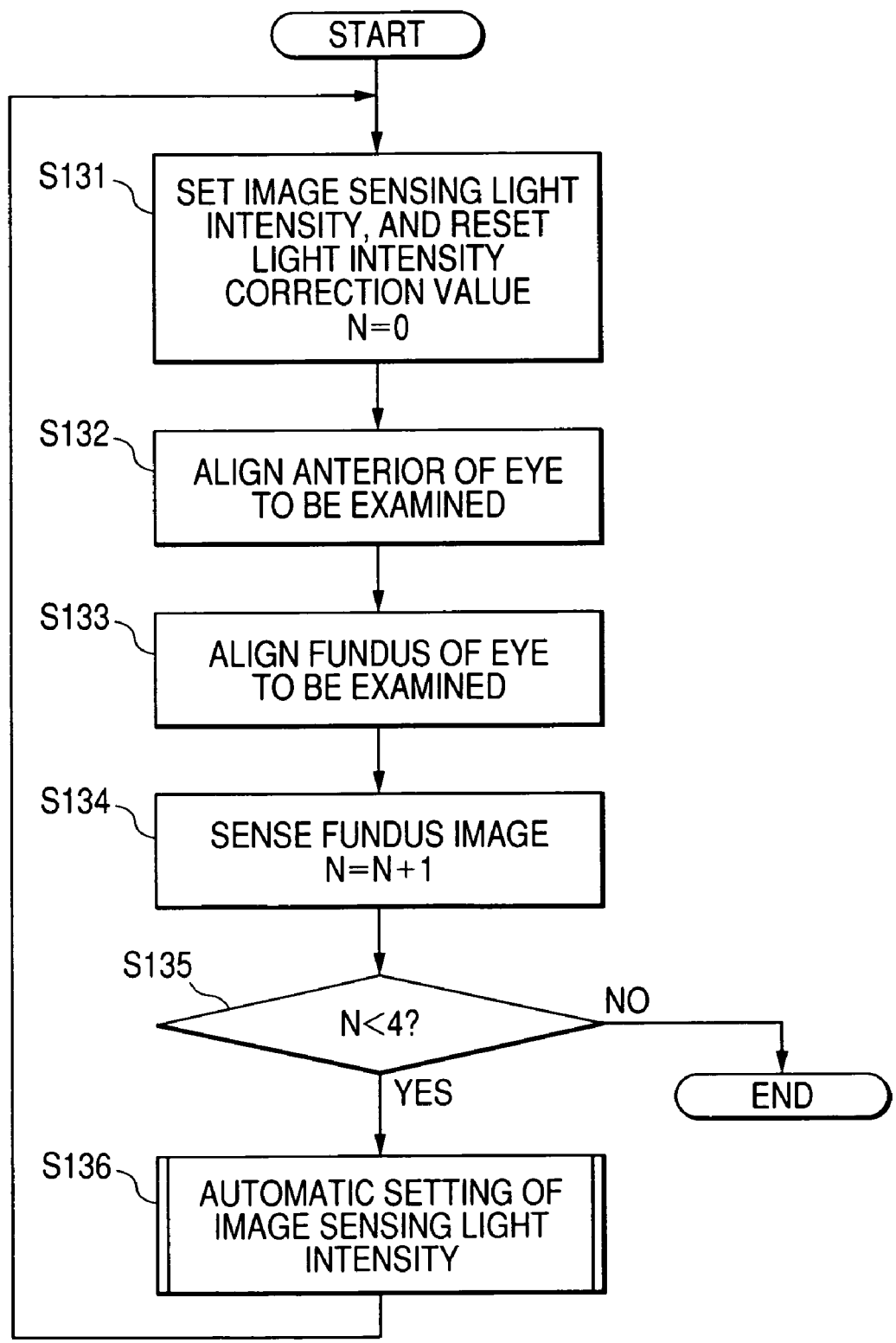
FIG. 18 being an operation flowchart of an eighth embodiment.

FIG. 18 shows an operation flow chart of an eighth embodiment for performing the automatic setting of image sensing light intensity at the time of the next image sensing within the limits of a predetermined number of images.

In a fundus examination, multiple times of image sensing, such as wide-angle image sensing, and enlarging image sensing of a characteristic region such as a papilla region for performing a glaucoma diagnosis, may be performed for the same eye E to be examined. At this time, generally, a number of images every eye E to be examined is the same, for example, an example that a first image is set for a posterior part of a fundus of eye and a second image is set for a papilla region, these images are set for both eyes, and hence, four images are sensed totally will be explained.

(Step S131) In advance of image sensing, the number of images of the same eye E to be examined, that is, four images in this example are set from an number of images setting unit to the image sensing light intensity setting unit 108, and a light intensity correction value and a number-of-image counter N are reset.

(Step S132) The alignment of an anterior segment of the eye E to be examined with the optical axis of the fundus camera 103 is performed in the anterior observing state.

(Step S133) It is changed to the fundus observing state, and work distance adjustment and focus adjustment with the fundus Er of eye are performed. An image sensing angle is set, for example, in wide-angle image sensing in the case of a first image of a right eye, and an optical system is changed for enlarging image sensing in the case of a second image. Also in the case of a left eye, similarly, it is set in wide-angle image sensing in the case of a third image, and it is changed for enlarging image sensing in the case of a fourth image.

(Step S134) The sensing switch 106 is pushed and fundus image sensing is performed. The sensed images are displayed on the TV monitor 112, and the number-of-image counter N counts up.

(Step S135) It is determined whether the number-of-image counter N is less than four images. When the count is less than four images, it goes to step S136, and when it is four images, it is completed to END.

(Step S136) The light intensity at the time of the next image sensing is corrected. Similarly to other embodiments shown above, correction of image sensing light intensity is performed.

Although the above-mentioned three methods can be applied to the change of image sensing light intensity, a changing amount may be changed by the three methods when the image sensing methods differ like the third embodiment. In this case, a changing amount may be multiplied by a coefficient such as 0.9 every image sensing method.

Embodiment 9

Figure 19:
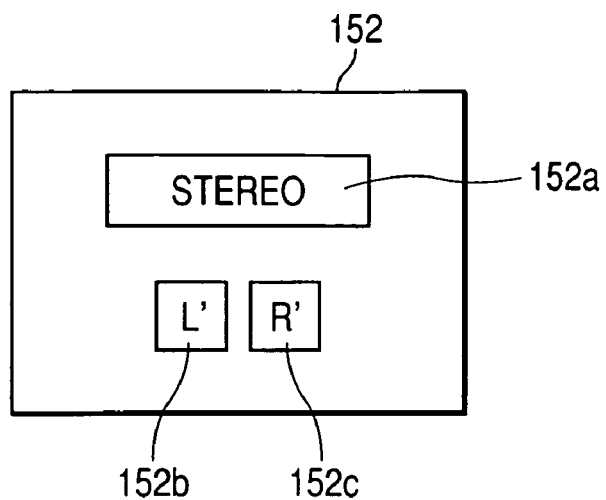
FIG. 19 being a structural diagram of a solid sensing switch.

FIG. 19 shows the stereo photographing setting unit 152 changing a mode to solid image sensing in a ninth embodiment, which is a switch 152a changing a mode to a solid image sensing mode. Then, a switch 152b is pushed when a left image of a stereo pair is sensed, and a switch 152c is pushed when a right image is sensed. States of these switches 152b and 152c are written in a supplementary information area of the sensed images, and the sensed images are arranges and displays right and left when being displayed on the TV monitor 112. An observer looking at a stereoscopic image observes it with putting on a glass for solid observation.

Figure 20:
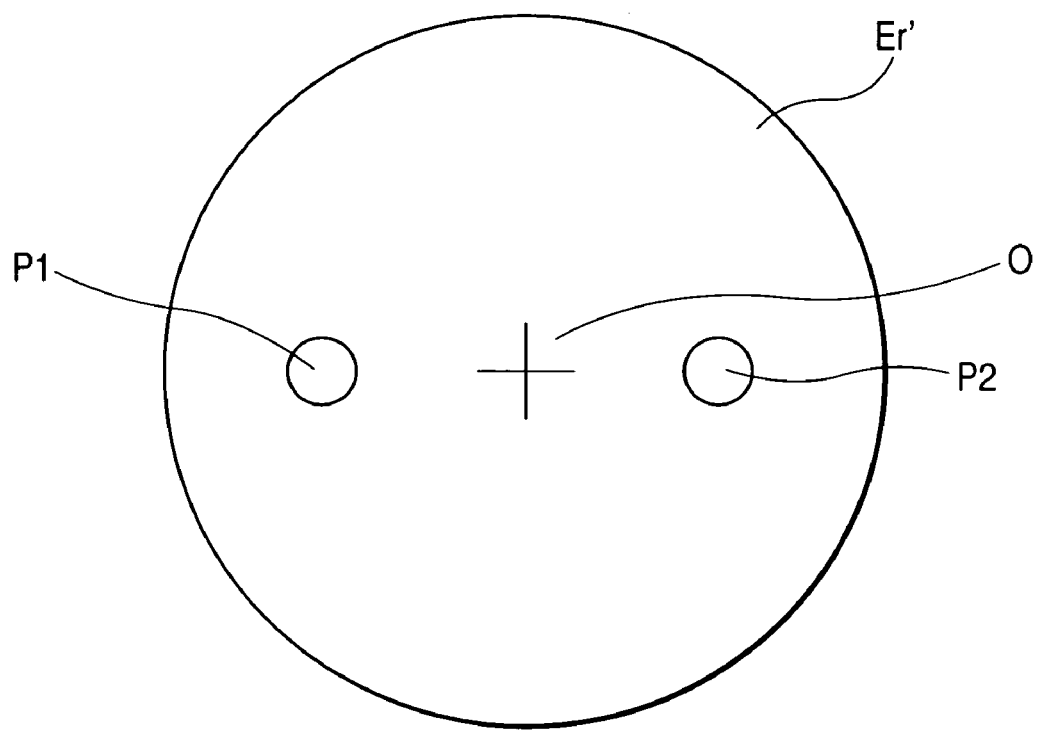
FIG. 20 being an explanatory diagram of an observed image at the time of solid image sensing.

FIG. 20 is an explanatory diagram of an eye to be examined and indices for solid image sensing which are displayed on the observing monitor 110. A fundus image Er' is displayed with an image sensing optical axis O which is a character and is electrically synthesized with a video signal, and bright spots P1 and P2 which are projected on the cornea Ec of the eye E to be examined are displayed simultaneously.

The switch 152a is pushed to change the mode to the solid image sensing, and when the switch 152b turns on first, the bright spot P1 blinks. A camera person moves the stage unit 102 with operating the operation rod 105 right and left so that the image sensing optical axis O may be superimposed on the bright spot P1, and senses images. Next, when the switch 152c is pushed, the bright spot P2 l blinks. Hence, the camera person moves the stage unit 102 so that the image sensing optical axis O may be superimposed on the bright spot P2, and senses images for a stereoscopic image.

Figure 21:
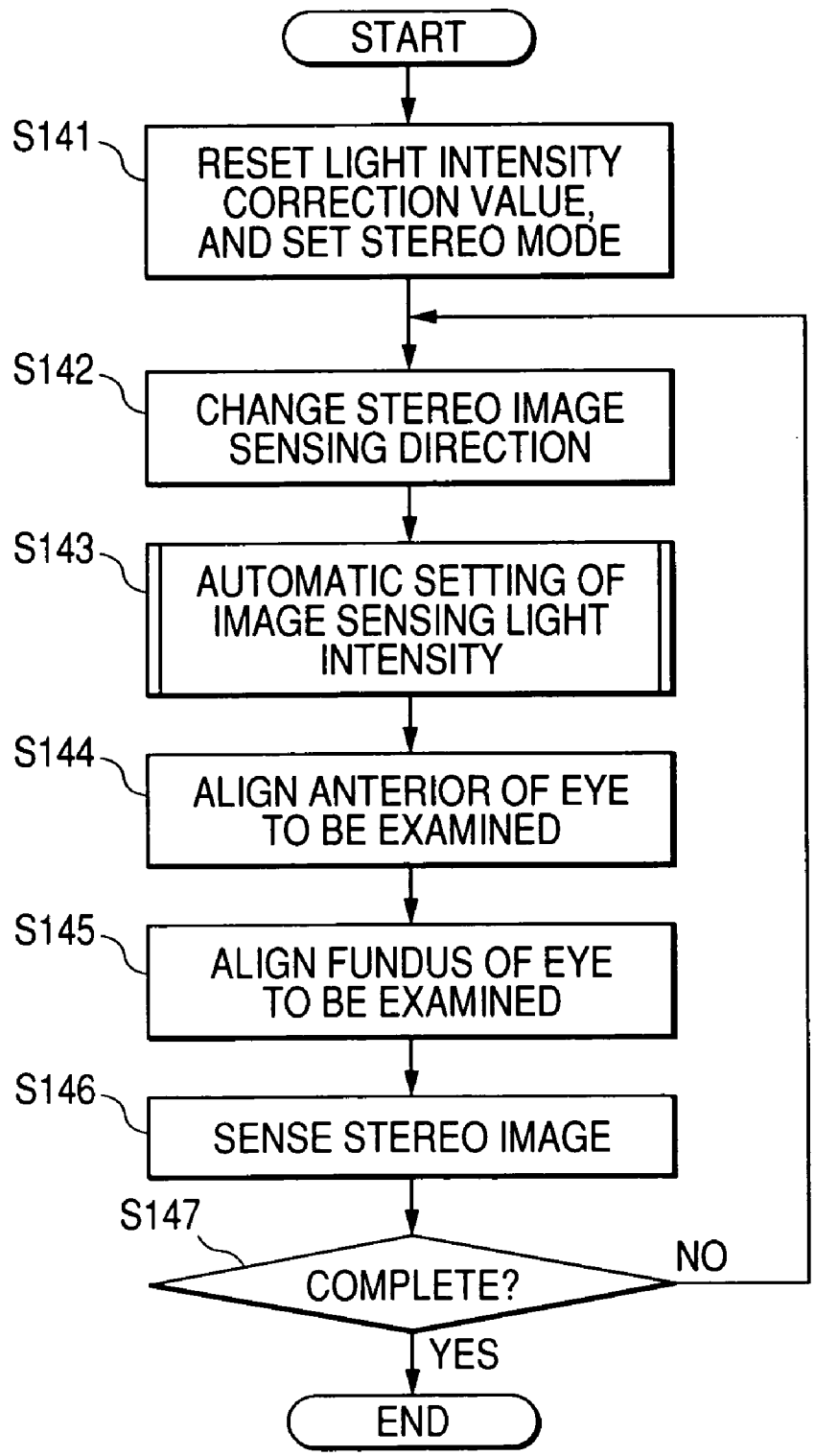
FIG. 21 being an operation flowchart of a ninth embodiment.

FIG. 21 is an operation flowchart of a ninth embodiment. In the solid image sensing, a pair of two images is sensed sequentially with being shifted by a predetermined base length within a diameter of a pupil of the eye E to be examined, and image sensing light intensity is set automatically at the time of second image sensing.

(Step S141) In advance of image sensing, light intensity is set, a light intensity correction value is reset, and the mode is changed to a solid image sensing mode.

(Step S142) A direction of stereo image sensing is changed by pushing the switch 152b or 152c which are shown in FIG. 19.

(Step S143) When first image sensing is performed, image sensing light intensity is set automatically, which performs light intensity correction for the second and later. This correction is the same as that in the above-described other embodiments.

(Step S144) The alignment of the eye E to be examined with the optical axis of the fundus camera 103 is performed in the anterior segment observing state.

(Step S145) It is changed to the fundus observing state, and work distance adjustment and focus adjustment are performed. Since it is the stereo image sensing mode, the stage unit 102 is deflected a little by operating the operation rod 105 so that the image sensing optical axis O showing a center of the optical axis may coincide with the bright spot P1 (or P2) which is blinking.

(Step S146) The sensing switch 106 is pushed and a pair of fundus images for a stereo image is sensed.

(Step S147) Then, a second pair of images for a stereo image is sensed, that is, the image sensing of another eye is performed by changing the right or left eye, and the image sensing is completed.

In addition, in this case, it is possible to adjust the variance; of an opening degree of the pupil Ep by the image sensing optical axis O changing by the base length.

Embodiment 10

Figure 22:
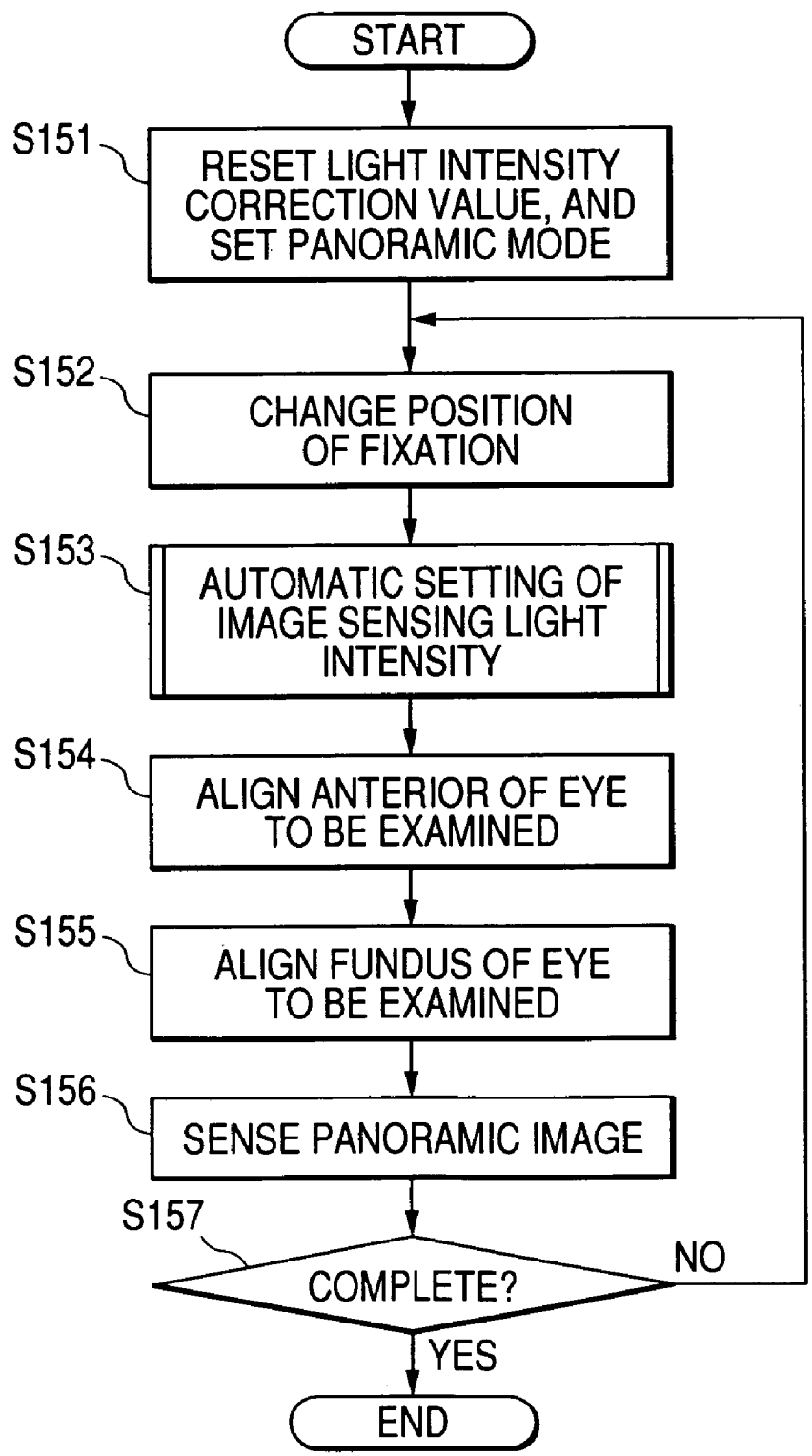
FIG. 22 being an operation flowchart of a tenth embodiment.

FIG. 22 is an operation flow chart of a tenth embodiment in the case of setting image sensing light intensity at the time of the second and later automatically when panoramic image sensing is performed.

In the case of performing panoramic image sensing, the panoramic image sensing setting unit 153 is pushed, and it is changed to a panoramic image sensing mode. Next, a fixation lamp position changing switch which is provided in the stage unit 102 for changing a fixation position of the fundus Er of eye and which is not shown is changed every image sensing sequentially, and a predetermined number of images are sensed. Panoramic image sensing mode information, fixation position information, and right or left eye information are sent to the sensed image recording unit 111 and are written in a supplementary information area of the sensed images, and are used at the time of pasting processing.

(Step S151) In advance of image sensing, light intensity is set, a light intensity correction value is reset, and the mode is changed to the panoramic image sensing mode.

(Step S152) The fixation lamp position changing switch is pushed for panoramic image sensing so that a fixation direction of the eye E to be examined is changed.

(Step S153) Light intensity correction is not performed at first image sensing, but the light intensity correction is performed at the time of second image sensing and later. This correction is the same as that in the above-described other embodiments.

(Step S154) The alignment of the eye E to be examined with the optical axis of the fundus camera 103 is performed in the anterior segment observing state.

(Step S155) It is changed to the fundus observing state, and work distance adjustment and focus adjustment are performed. Since the mode is the panoramic image sensing mode, a position of the fundus Er of eye is shifted every image sensing.

(Step S156) The sensing switch 106 is pushed and panoramic fundus image sensing is performed.

(Step S157) Then, a predetermined number of images for a panoramic image are sensed, the image sensing of another eye is performed by changing the right or left eye, and the image sensing is completed. When changed to another eye, a fixation lamp position returns to an initial position.

Also in the case of this panoramic image sensing, it is possible to change the changing amount of light intensity by the above-described three methods similarly to the case of usual image sensing. In addition, the changing amount may be multiplied by a coefficient such as 0.9 every image sensing method.

In each embodiment mentioned above, an example of setting the next image sensing light intensity automatically is explained. In addition, when the light intensity correction which was performed by the automatic setting of image sensing light intensity is reset when the person S to be examined is changed so that an ID for identifying the person S to be examined is updated, it is possible to automate the light intensity correction resetting operation at the time when image sensing is completed and the image sensing of the next person S to be examined is started. This ID is inputted from a ten key provided in the stage unit 102, or is inputted from a magnetic card reader connected to the base unit 101. The inputted ID is sent to the sensed image recording unit 111 with the sensed images, and is written in the supplementary information storage area of an image file.

In addition, in each embodiment mentioned above, the next and later image sensing light intensity is made to be set automatically. But, it is also good to display a care mark or the like, which prompts light intensity change simply, on the observing monitor 110, and to erase this care mark when a camera person performs light intensity adjustment by operating the image sensing light intensity setting unit 108 in the stage unit 102. In addition, the timing of displaying the care mark is a time of determining the correction of the light intensity mentioned above.

As explained above, according to the present invention, it is possible to provide a fundus image sensing apparatus which reduces an adjustment burden of image sensing light intensity.

In addition, it is not necessary to say that the object of the present invention can be also achieved by supplying a storage medium, which stores the program code of the software which realizes functions of apparatuses or systems of the embodiments, to apparatuses or systems, and by each computer (CPU or MPU) of the apparatuses or systems reading and executing the program code stored in the storage medium. In this case, since the program code itself read from the recording medium achieves the functions of the above-mentioned embodiments, the recording medium, recording the program code, and the program code concerned constitutes the present invention.

What are used as the recording medium for supplying the program code are, for example, ROM, a floppy disk (trademark), a hard disk, an optical disk, a magneto-optical disk, CD-ROM, CD-R, a magnetic tape, and a non-volatile memory card.

In addition, what are naturally included in aspects of the present invention are not only the case that the functions of the embodiments mentioned above are achieved by executing the program code which each computer reads, but also the case that the functions of the above-mentioned embodiments are achieved by a part or all of processing being executed by an OS or the like, which is working on the computer, on the basis of instructions of the program code.

Furthermore, it is not necessary to say that what is included in an aspect of the present invention is also the case that the functions of the above-mentioned embodiments are achieved by writing the program code, read from the recording medium, in memory provided in a feature expansion board inserted in each computer, or a feature expansion unit connected to each computer, and a part or all of actual processing being executed by each CPU or the like, which is provided in the feature expansion board or feature expansion unit, on the basis of instructions of the program code.

When the present invention is applied to such a program or a storage medium which stores the program concerned, the program concerned is constituted of program codes corresponding to, for example, the above-described operation flow chart.

As many apparently widely different embodiments of the present invention can be made without departing from the spirit and scope thereof, it is to be understood that the invention is not limited to the specific embodiments thereof except as defined in the claims.

This application claims priorities from Japanese Patent Application Nos. 2004-283468 filed on Sep. 29, 2004, and 2005-179160 filed on Jun. 20, 2005,. which are hereby incorporated by reference herein.

What is claimed is:

1. An ophthalmological photographing apparatus for photographing a fundus image of an eye to be examined multiple times, comprising:
    image sensing means for photographing the fundus image and converting the fundus image into a digital signal;
    a photographing light source for illuminating a fundus of the eye to be examined;
    an image sensing optical system for illuminating the fundus image of eye to be examined at the time of photographing fundus image, by light from the photographing light source;
    setting means for setting the light intensity of light from the photographing light source, at a first time of photographing the fundus image; and
    control means for controlling the photographing light source so that the light intensity at a second time of photographing is larger than that at the first time of photographing, which is set by the setting means,
    wherein the control means determine the light intensity of the illumination light from the photographing light source at the second time of photographing, on the basis of a calculation result executed using the light intensity of the illumination light at the time of photographing and a value calculated on the basis of a diameter of pupil of the eye to be examined.

2. An ophthalmological photographing apparatus according to claim 1, further comprising:
    an observing light source for illuminating an anterior segment so as to observe the anterior segment; and
    switching means for switching the illumination light between light provided from the photographing light source and the light provided from the observing light source,
    wherein the control means set the light intensity at the time of photographing on the basis of switching operation of the switching means.

3. An ophthalmological photographing apparatus according to claim 1, further comprising number-of-images storing means for storing a number of images each of which is photographed by the image sensing means,
    wherein the control means set the light intensity of the illumination light from the photographing light source on the basis of the number of images stored in the number-of-images storing means.

4. An ophthalmological photographing apparatus according to claim 1, further comprising person-to-be-examined identification information input means of inputting person-to-be-examined identification information,
    wherein the control means set the light intensity of the illumination light from photographing light source on the basis of presence of an input the person-to-be-examined identification information input means.

5. An ophthalmological photographing apparatus according to claim 1, further comprising right-or-left-eye detection means for detecting whether an eye being examined is right or left eye,
    wherein the control means set the light intensity of the illumination light from the photographing light source at the second time of photographing in accordance with a case where the eye to be examined at the second time photographing is the same eye examined at the time of the first time photographing or a case where the eye to be examined at the second time photographing is different from the eye examined at the time of the first time photographing.

6. An ophthalmological photographing apparatus for photographing a fundus image of an eye to be examined multiple times, comprising:
    image sensing means for photographing the fundus image and converting the fundus image into a digital signal;
    a photographing light source for illuminating a fundus of the eye to be examined at the time of photographing fundus image;
    setting means for setting the light intensity of light from the photographing light source, at a first time of photographing the fundus image; and
    control means for controlling the photographing light source so that the light intensity at a second time of photographing is larger than that at the first time of photographing, which is set by the setting means,
    wherein the control means set the light intensity at the second time of photographing on the basis of the light intensity at the first time of photographing,
    wherein the control means determine the light intensity of the illumination from the photographing light source at the second time of photographing, on the basis of a calculation result executed using the light intensity of the illumination light at the time of photographing and a value calculated on the basis of a diameter of pupil of the eye to be examined.

7. An ophthalmological photographing apparatus according to claim 6, further comprising memory means for storing a table designating a relation between the light intensity at the first time of photographing and the light intensity at a second time of photographing,
    wherein the control means set the light intensity at the second time of photographing on the basis of the light intensity at the first time of photographing, and the table stored in the memory means.

8. An ophthalmological photographing apparatus according to claim 1, wherein the control means determine the light intensity of the illumination light from the photographing light source at the second time of photographing, on the basis of a calculation result executed using 1) the light intensity of the illumination light at the first time of photographing and 2) a table presenting a relation between the light intensity of the photographing light source and a number of times of photographing.

* * * * *